United States Patent
Vaidya et al.

(10) Patent No.: US 10,839,513 B2
(45) Date of Patent: Nov. 17, 2020

(54) DISTINGUISHING HYPERPROGRESSION FROM OTHER RESPONSE PATTERNS TO PD1/PD-L1 INHIBITORS IN NON-SMALL CELL LUNG CANCER WITH PRE-THERAPY RADIOMIC FEATURES

(71) Applicant: Case Western Reserve University, Cleveland, OH (US)

(72) Inventors: Pranjal Vaidya, Cleveland, OH (US); Kaustav Bera, Cleveland, OH (US); Vamsidhar Velcheti, Pepper Pike, OH (US); Anant Madabhushi, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 66 days.

(21) Appl. No.: 16/297,889

(22) Filed: Mar. 11, 2019

(65) Prior Publication Data
US 2019/0347789 A1  Nov. 14, 2019

Related U.S. Application Data

(60) Provisional application No. 62/670,054, filed on May 11, 2018.

(51) Int. Cl.
*G06T 7/00* (2017.01)
*G06T 7/11* (2017.01)
(Continued)

(52) U.S. Cl.
CPC .......... *G06T 7/0012* (2013.01); *G06K 9/6228* (2013.01); *G06K 9/6262* (2013.01);
(Continued)

(58) Field of Classification Search
CPC ......... G06T 7/0012; G06T 7/136; G06T 7/11; G06T 2207/10081; G06T 2207/20076;
(Continued)

(56) References Cited

U.S. PATENT DOCUMENTS

2015/0254840 A1* 9/2015 Madabhushi ............. G06T 7/45
382/131
2018/0247410 A1* 8/2018 Madabhushi ........ G06K 9/6277
(Continued)

*Primary Examiner* — Ping Y Hsieh
(74) *Attorney, Agent, or Firm* — Eschweiler & Potashnik, LLC

(57) ABSTRACT

Embodiments access a pre-immunotherapy image of tissue demonstrating NSCLC including a tumor and a peritumoral region; extract a first set of radiomic features from the image; provide the first set of radiomic features to a first machine learning classifier; receive a first probability from the first classifier that the tissue is hyperprogressor (HP) or non-responder (R); if the first probability that the tissue is within a threshold: generate a first classification of the ROT as HP or non-R based on the first probability; if the first probability is not within the threshold: extract a second set of radiomic features from the peritumoral region and provide the second set to a second machine learning classifier; receive a second probability from the second classifier that the tissue is HP or R; generate a second classification of the tissue as HP or R based on the second probability; and display the classification.

20 Claims, 14 Drawing Sheets

(51) Int. Cl.
  *G06T 7/136* (2017.01)
  *G06K 9/62* (2006.01)
  *G16H 30/40* (2018.01)
  *G06N 20/20* (2019.01)
  *G06N 7/00* (2006.01)

(52) U.S. Cl.
  CPC ............ *G06N 7/005* (2013.01); *G06N 20/20* (2019.01); *G06T 7/11* (2017.01); *G06T 7/136* (2017.01); *G16H 30/40* (2018.01); *G06T 2207/10081* (2013.01); *G06T 2207/20076* (2013.01); *G06T 2207/20081* (2013.01); *G06T 2207/20152* (2013.01); *G06T 2207/30061* (2013.01); *G06T 2207/30096* (2013.01)

(58) Field of Classification Search
  CPC . G06T 2207/20081; G06T 2207/20152; G06T 2207/30061; G06T 2207/30096; G06N 20/20; G06N 7/005; G16H 30/40; G06K 9/6228; G06K 9/6262
  See application file for complete search history.

(56) References Cited

U.S. PATENT DOCUMENTS

| | | | |
|---|---|---|---|
| 2018/0253591 A1* | 9/2018 | Madabhushi | G06K 9/00147 |
| 2018/0276498 A1* | 9/2018 | Madabhushi | G06T 7/11 |
| 2019/0259156 A1* | 8/2019 | Madabhushi | G16H 50/70 |
| 2019/0266727 A1* | 8/2019 | Piron | G06T 7/0016 |
| 2020/0051246 A1* | 2/2020 | Carmi | A61B 6/037 |

* cited by examiner

910

920

1410

DISTINGUISHING HYPERPROGRESSION FROM OTHER RESPONSE PATTERNS TO PD1/PD-L1 INHIBITORS IN NON-SMALL CELL LUNG CANCER WITH PRE-THERAPY RADIOMIC FEATURES

CROSS REFERENCE TO RELATED APPLICATIONS

This application claims the benefit of United States Provisional Application 62/670,054 filed May 11, 2018, which is incorporated by reference herein in its entirety.

FEDERAL FUNDING NOTICE

This invention was made with government support under grants 1U24CA199374-01, R01CA202752-01A1, R01CA208236-01A1, R01CA216579-01A1, R01CA220581-01A1, and 1 C06RR12463-01 awarded by the National Institutes of Health. Also award W81XWH-16-1-0329 awarded by the Department of Defense. The government has certain rights in the invention.

BACKGROUND

Treatment with immune checkpoint inhibitors (ICI) can lead to durable response in a fraction of patients with advanced non-small cell lung cancer (NSCLC). However, a majority of advanced stage NSCLC patients do not response to ICI. Furthermore, a subset of patients of patients treated with ICI experience a dramatic increase in tumor growth rate after ICI therapy. Hyperprogression is characterized by accelerated tumor growth rate after ICI therapy. The rate of hyperprogression may range from 9% to 16% of advanced stage NSCLC patients treated with ICIs. There are currently no clinically validated biomarkers to identify patients who will experience hyperprogression (HPs).

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
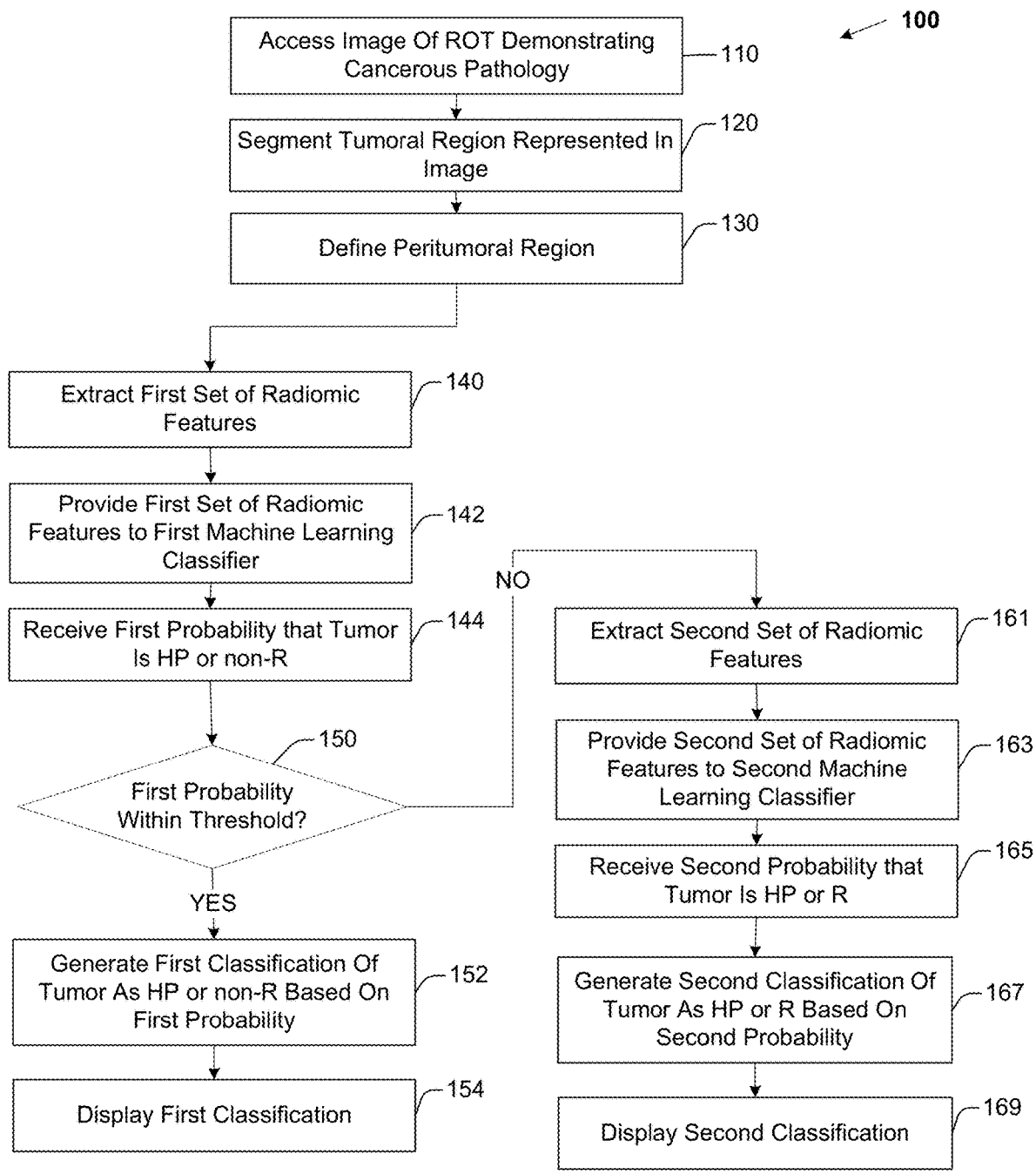
FIG. 1 illustrates a flow diagram of example operations for distinguishing patients who will experience hyperprogression from those who will respond or not respond to immunotherapy.

Hyperprogression in advanced stage non-small cell lung cancer (NSCLC) is the dramatic increase in tumor growth after immunotherapy treatment compared to baseline tumor growth rate. Patients who experience hyperprogression, known as hyperprogressors (HPs) may be identified as patients who have a time to treatment failure of <=2 months, a>=2 fold increase in tumor growth rate after starting immunotherapy (e.g., ICI), and a >=2 fold increase in tumor burden after starting immunotherapy. The estimated proportion of the advanced stage NSCLC patient population that will experience hyperprogression ranges from 8% to 12%, to as high as 9% to 16%. There are currently no clinically validated biomarkers to identify HPs prior to ICI therapy.

Embodiments distinguish patients who are at risk of hyperprogression from those who either respond or do not respond to immunotherapy. Embodiments extract a set of radiomic features from computed tomography (CT) imagery of a region of tissue demonstrating NSCLC. The set of radiomic features may include tumoral radiomic features, or peri-tumoral radiomic features. Embodiments provide the set of radiomic features to a machine learning classifier trained to distinguish patients who are at risk of hyperprogression from those who either respond to immunotherapy or do not respond to immunotherapy. Embodiments receive, from the machine learning classifier, a probability that the patient of whom the CT imagery is acquired will experience hyperprogression. The machine learning classifier computes the probability based, at least in part, on the set of radiomic features. Embodiments further classify the patient as a hyperprogressor or responder or non-responder based, at least in part, on the probability. Embodiments further include training the machine learning classifier to distinguish patients who are at risk of hyperprogression from those who either respond to immunotherapy or do not respond to immunotherapy.

In one embodiment, the charts of a cohort of 336 patients with advanced NSCLC who received monotherapy with a PD1/PD-L1 inhibitor were reviewed. A PD1/PD-L1 inhibitor (i.e., immunotherapy agent) may include, for example, Nivolumab, pembrolizumab, or ateziolizumab. For patients in the cohort who developed progressive disease within three cycles of ICI therapy, pre-baseline, baseline, and post-treatment CT imagery of a region of tissue demonstrating NSCLC were acquired of the patients and used to compute tumor growth kinetics (TGK) for each patient, respectively. The region of tissue includes a tumoral region. The ratio of pre-treatment TGK and post-treatment TGK is used to identify HPs, where the ratio >=2, and N=28. Intratumoral and peritumoral radiomic features were extracted from the baseline CT imagery for HPs and for non-responders (NRs), and responders (Rs). In a training cohort, a total of 925 radiomic features that were differentially expressed in HPs vs. Rs (N=28) and HPs vs. NRs (N=28) were analyzed.

In this example, pre-baseline and baseline CT imagery is acquired pre-treatment (i.e., pre-immunotherapy). The pre-baseline and baseline CT imagery are acquired from two to five months apart from each other. The post-treatment CT imagery is acquired during treatment after at least the first two cycles of immunotherapy treatment administered to the patient.

In this example, computing TGK for a patient includes identifying target lesions (e.g., tumors) within the region of tissue. Target lesions may be identified per the RECIST criteria, where the target lesion has a diameter >=10 mm, across up to five organs, with no more than two target lesions per organ. Computing TGK also includes computing the sum of the diameters of the largest target lesions in the pre-baseline imagery and the baseline imagery, as well as in the post-treatment imagery. Embodiments compute TGK pre-immunotherapy using the pre-baseline and baseline CT imagery. TGK pre-immunotherapy may be computed as:

$$TGK_{pre} = \frac{Sum_{baseline} - Sum_{pre\text{-}baseline}}{\text{Time between scans}},$$

where the time between scans is the time between the pre-baseline and baseline scans. TGK post-immunotherapy may be computed as:

$$TGK_{post} = \frac{Sum_{post\text{-}treatment} - Sum_{baseline}}{\text{Time between scans}},$$

where the time between scans is the time between the baseline scan and the post-treatment scan. Computing the TGK further includes computing the ratio of $TGK_{post}$ to $TGK_{pre}$. Where the ratio of $TGK_{post}$ to $TGK_{pre}$ is >1, the patient is classified as a progressor. Where the ratio of $TGK_{post}$ to $TGK_{pre}$ is >=2, the patient is classified as a hyperprogressor. In other embodiments, other techniques may be employed to classify the patient as a hyperprogressor.

Figure 13:
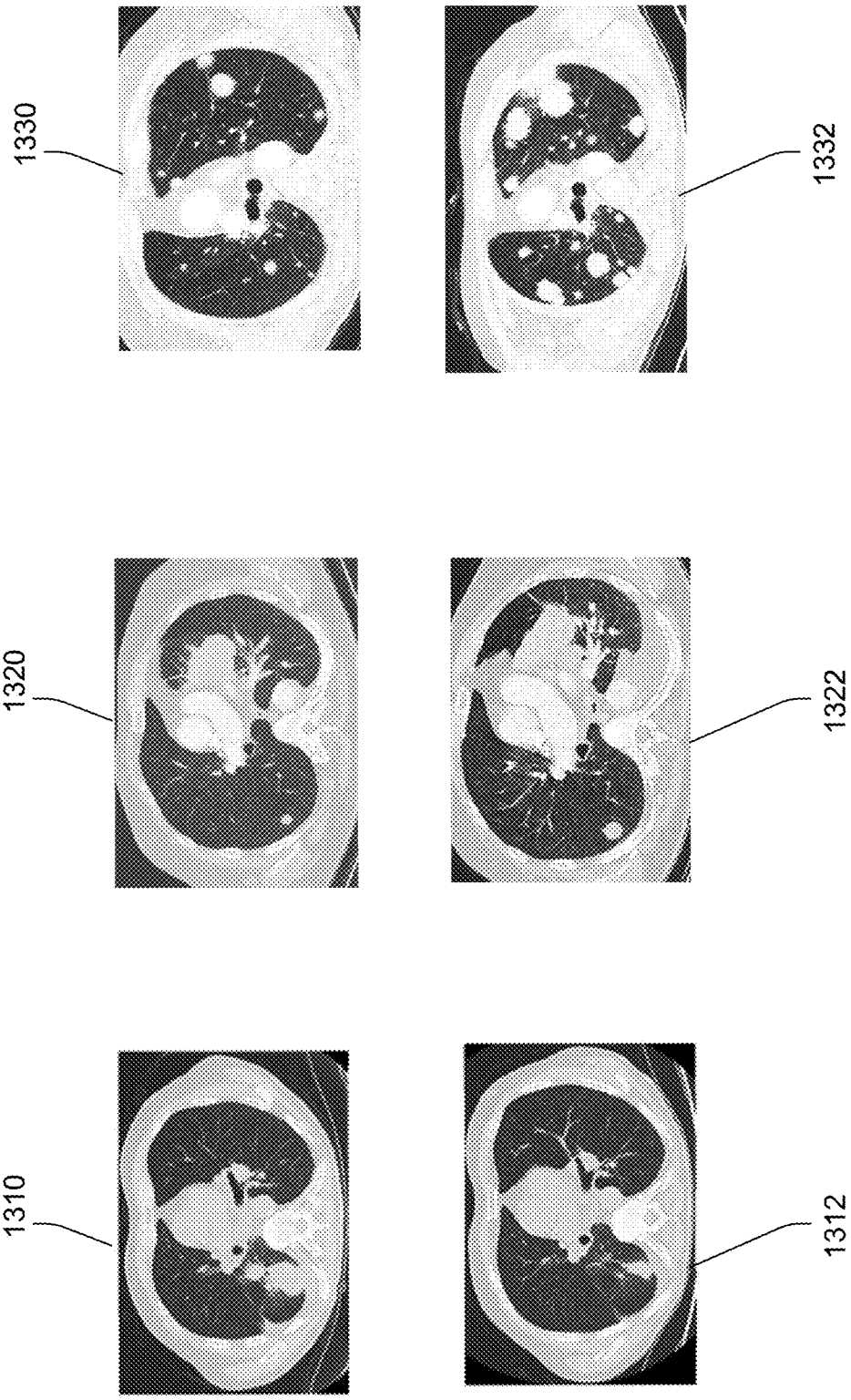
FIG. 13 illustrates computer tomography (CT) imagery of a responder to immunotherapy, a non-responder to immunotherapy, and hyperprogressor.

FIG. 13 illustrates CT imagery of a responder, a non-responder, and hyperprogressor. CT imagery of responder acquired at a first time is illustrated at 1310, and acquired at a second, later time at 1312. CT imagery of non-responder acquired at a first time is illustrated at 1320, and at a second, later time at 1322. CT imagery of hyperprogressor acquired at a first time is illustrated at 1330, and at a second, later time at 1332.

In this example, the top five most predictive radiomic features were identified from among the total of 925 radiomic features using a minimum redundancy maximum relevance (mRMR) feature selection approach. For differentiating hyperprogressors from responders, the top five most predictive radiomic features include a kurtosis of intratumoral Laws spot-spot feature, a range of a peritumoral Gabor feature with frequency of 0 and theta of 0 extracted from a 3 mm-6 mm peritumoral region, a kurtosis of a Laws level-level feature extracted from a 3 mm-6 mm peritumoral region, a mean of a Laws ripple-edge feature extracted from a 3 mm-6 mm peritumoral region, and a mean of a Laws ripple-edge feature extracted from a 9 mm-12 mm peritumoral region. For differentiating hyperprogressors from non-responders, the top five most predictive radiomic features include a standard deviation of a Laws level-spot feature extracted from a 0 mm-3 mm peritumoral region, a range of a Gabor feature with frequency of 0 and theta of 0 extracted from a 3 mm-6 mm peritumoral region, a kurtosis of a Gabor feature with a frequency of 2 and theta of 0 extracted from a 3 mm-6 mm peritumoral region, a skewness of a Haralick correlation feature extracted from a 3 mm-6 mm peritumoral region, and a kurtosis of a co-occurrence of local anisotropic gradient orientations entropy inertia feature extracted from a 3 mm-6 mm peritumoral region. In another embodiment, the top five most discriminative features may include other, different radiomic features. While the top five most discriminative features are described in this example, other different numbers of features may be selected.

Figure 10:
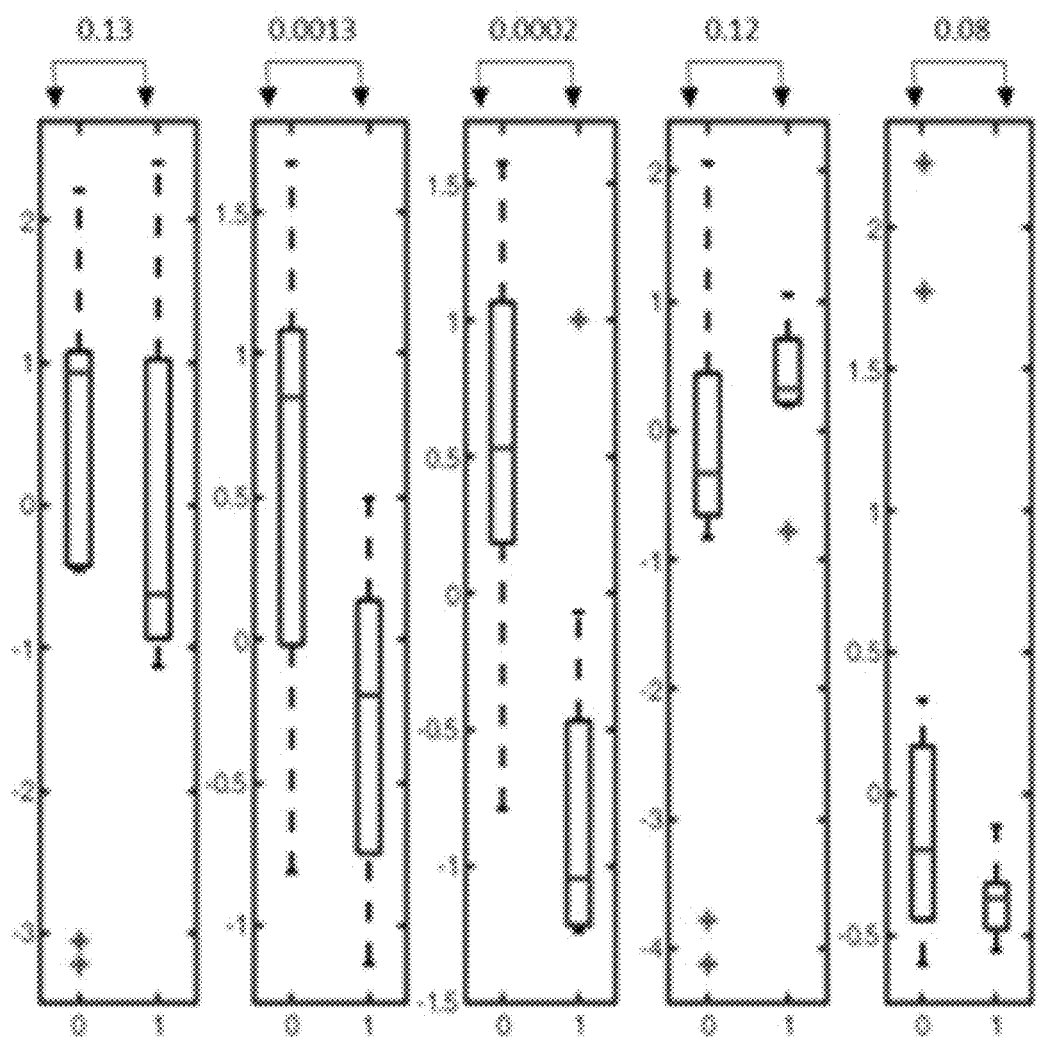
FIG. 10 is a box plot of discriminative radiomic features for distinguishing hyperprogressors from non-responders according to embodiments.

FIG. 10 illustrates a box plot 1010 of the top five most discriminative radiomic features for distinguishing hyperprogressors from non-responders according to embodiments. In FIG. 10, each box and whisker plot represents feature distribution in HP vs. non-responders.

Figure 11:
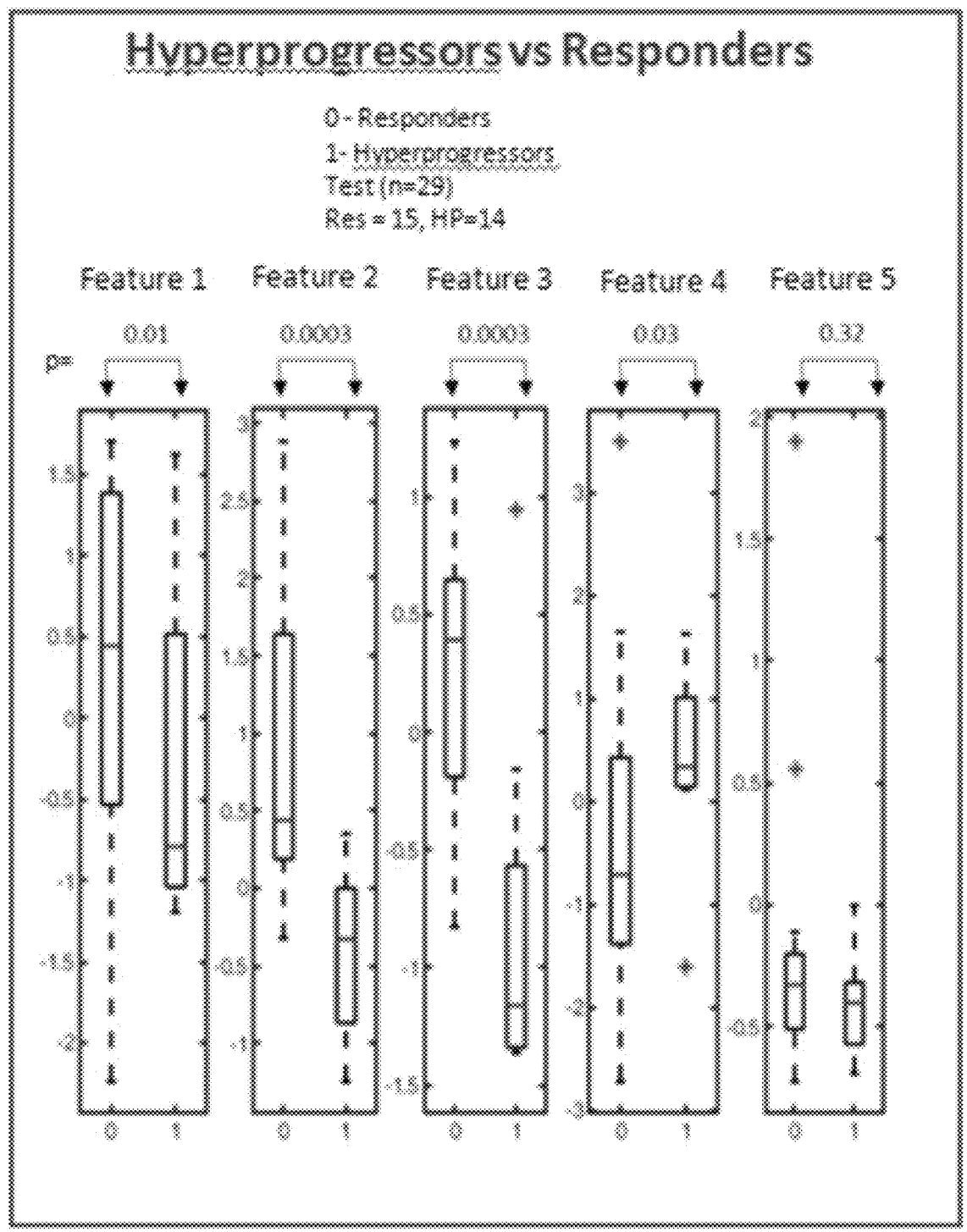
FIG. 11 is a box plot of discriminative radiomic features for distinguishing hyperprogressors from responders according to embodiments.

FIG. 11 illustrates a box plot 1110 of the top five most discriminative radiomic features for distinguishing hyperprogressors from responders according to embodiments. In FIG. 11, each box and whisker plot represents feature distribution in HP vs. responders.

Embodiments define a peritumoral region based on a morphological transformation of the tumoral boundary. A peritumoral region may be defined as the region surrounding the tumoral region out to a distance. For example, in one embodiment, the peritumoral region may be the region extending 2 mm from the tumoral boundary. In another embodiment, the peritumoral region may be the region extending 6 mm from the tumoral boundary. The peritumoral region may be defined by a distance measured in mm, as described, or in other units, including pixels.

Figure 7A:
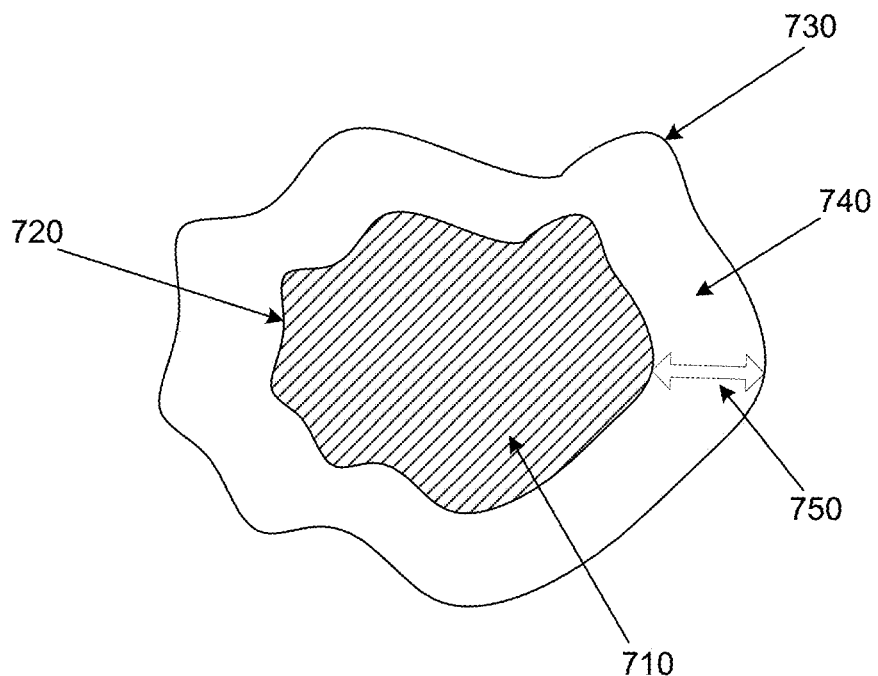
FIGS. 7A and 7B illustrate tumoral and peritumoral regions.

FIG. 7A illustrates an example peritumoral region 740 associated with an NSCLC tumor 710. Peritumoral region 740 is bounded by outer peritumoral boundary 730 and tumoral boundary 720. In one embodiment, example operations, methods, and apparatus morphologically dilate tumoral boundary 720 by an amount 750, resulting in the outer peritumoral boundary 730. Amount 750 may be, for example, 2 mm, 3 mm, 4 mm, 6 mm, 12 mm, 6 pixels, 8 pixels, or another, different amount.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary.

Figure 7B:
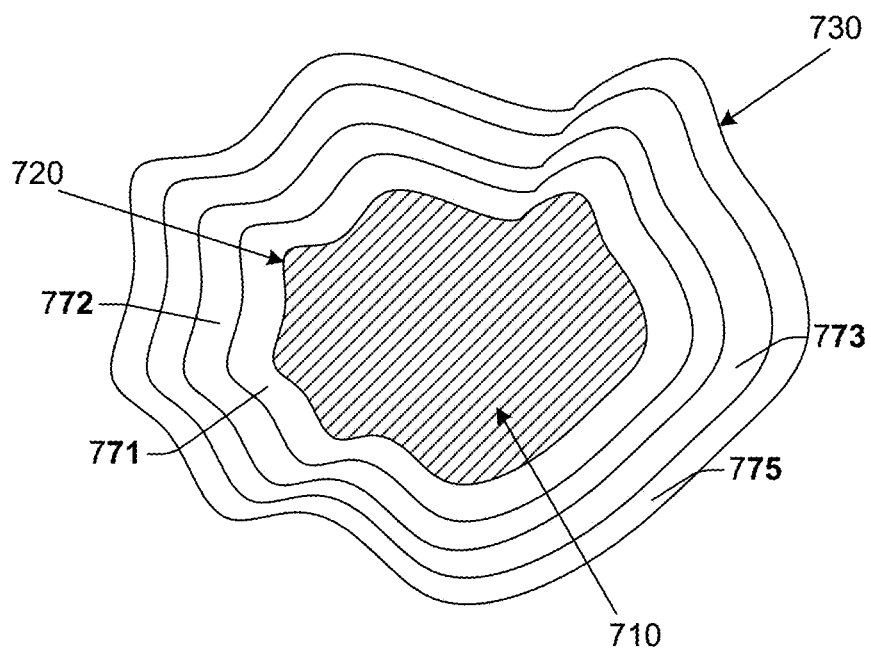

In one embodiment, the peritumoral region is defined using 3 mm annular rings defined about the boundary of the tumoral region out to a radius of 12 mm from the boundary. FIG. 7B illustrates an example peritumoral region that includes four annular rings 771, 772, 773, and 775 defined from the peritumoral boundary 720. Annular ring 771 extends from 0 mm to 3 mm from the tumoral boundary. Annular ring 772 extends from 3 mm to 6 mm from the tumoral boundary. Annular ring 773 extends from 6 mm to 9 mm from the tumoral boundary. Annular ring 775 extends from 9 mm from the tumoral boundary 720 to 12 mm from the tumoral boundary 720. In another embodiment, other annular ring sizes, radii, numbers of rings, or techniques may be employed to define the peritumoral region.

In this example, a linear discriminant analysis (LDA) machine learning classifier is trained to distinguish patients who are at risk of hyperprogression from those who either respond to immunotherapy or do not respond to immunotherapy using the top five most predictive radiomic features. The performance of the top five most predictive radiomic features was validated using an independent testing set of HPs vs. Rs (N=28) and HPs vs. NRs (N=29). A first LDA classifier in this example distinguishes HPs vs. NRs with area under the receiver operative curve (AUC) of at least 0.80 with a sensitivity of 0.92. A second LDA classifier in this example distinguishes HPs vs. Rs with an AUC of at least 0.79 and a sensitivity of 0.85.

In this example, the set of patients who were HPs (N=28) includes 11 patients 65 years old or younger, and 17 patients older than 65 years. The set of patients who were HPs includes 18 male patients and 10 female patients. The set of patients who were HPs includes 5 patients who never smoked, 15 former smokers, and 8 current smokers. The set of patients who were HPs includes 17 demonstrating adenocarcinoma, 10 demonstrating squamous [NSCLC?], and 1 poorly differentiated patient. The set of patients who were HPs included 5 having the EGFR mutation, 3 with KRAS mutation, and 20 with no known mutations. The set of patients who were HPs included three who were treated first line of treatment with immunotherapy, sixteen with second line, five with third line, and four with fourth line immunotherapy. In this example, first line immunotherapy indicates that immunotherapy treatment was given before other forms of therapy (e.g., chemotherapy). Second, third, and fourth line indicates that the patient has received one, two, or three other types of therapy before immunotherapy.

Figure 8:
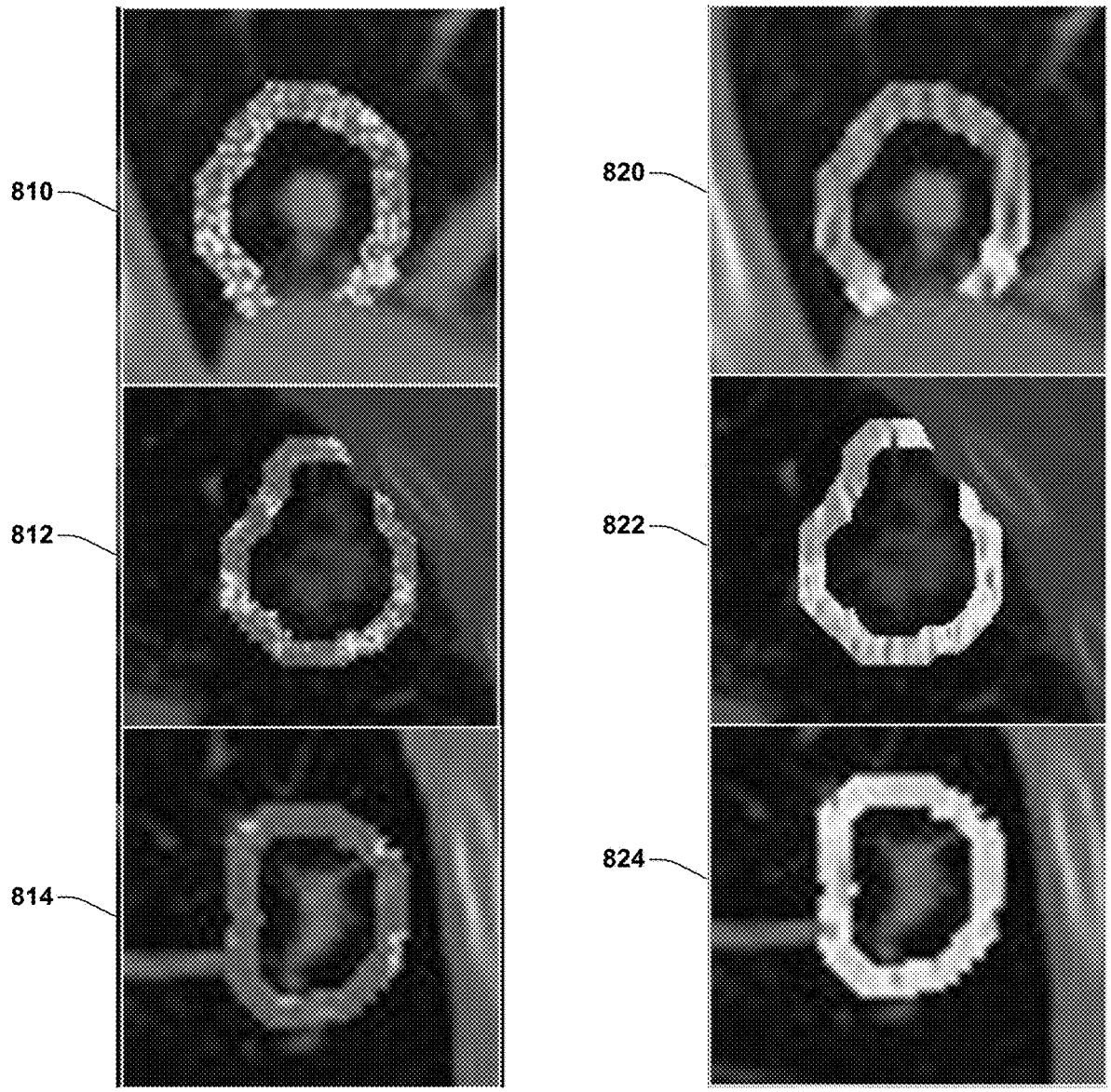
FIG. 8 illustrates radiomic features of a hyperprogressor, a responder, and a non-responder.

FIG. 8 illustrates radiomic features maps for responders, non-responders, and hyperprogressors. FIG. 8 includes, at 810, a radiomic feature map for a Laws feature extracted from a 3 mm to 6 mm annular ring of a responder. FIG. 8 includes, at 812, a radiomic feature map for a Laws feature extracted from a 3 mm to 6 mm annular ring of a non-responder. FIG. 8 includes, at 814, a radiomic feature map for a Laws feature extracted from a 3 mm to 6 mm annular ring of a hyperprogressor. FIG. 8 includes, at 820, a radiomic feature map for a Gabor feature extracted from a 3 mm to 6 mm annular ring of a responder. FIG. 8 includes, at 822, a radiomic feature map for a Gabor feature extracted from a 3 mm to 6 mm annular ring of a non-responder. FIG. 8 includes, at 824, a radiomic feature map for a Gabor feature extracted from a 3 mm to 6 mm annular ring of a hyperprogressor.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

An exemplary embodiment for classifying a region of tissue as a hyperprogressor, or as a responder or non-responder is now described. FIG. 1 illustrates an example flow diagram of operations 100 that may be performed by a processor for classifying a region of tissue as a hyperprogressor, or as a responder or non-responder. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

Operations 100 include, at 110, accessing a pre-immunotherapy treatment image of a region of tissue demonstrating cancerous pathology. The image includes a plurality of pixels, a pixel having an intensity. In one embodiment, the image is a pre-immunotherapy treatment digitized computed tomography (CT) image of a region of tissue demonstrating non-small cell lung cancer (NSCLC). In another embodiment, the image may be acquired using a different imaging modality (e.g., magnetic resonance imaging (MRI)). Accessing the image includes acquiring electronic data, reading from a computer file, receiving a computer file, reading from a computer memory, or other computerized activity that cannot be practically performed in the human mind.

Operations 100 also includes, at 120, defining a tumoral boundary by segmenting a tumoral region represented in the image. In one embodiment, defining the tumoral boundary by segmenting the tumoral region represented in the image includes automatically segmenting the tumoral region using a watershed approach. In another embodiment, other automated techniques may be employed to segment the tumoral region, including deep learning approaches. In another embodiment, the tumoral region has already been segmented prior to accessing the image at 110, and thus, in one embodiment, step 120 may be skipped. Defining the tumoral boundary includes acquiring electronic data, reading from a computer file, receiving a computer file, reading from a computer memory, or other computerized activity that cannot be practically performed in the human mind.

Operations 100 also includes, at 130, defining a peritumoral region based on the tumoral boundary. The peritumoral region includes a plurality of annular rings. In one embodiment, defining the peritumoral region based on the tumoral boundary includes dilating the tumoral boundary a threshold amount. The threshold amount is greater than zero. Dilating the tumoral boundary a threshold amount (e.g., 12 mm) defines a peritumoral boundary. In one embodiment, the tumoral boundary is dilated 12 mm from the tumoral boundary, and the resultant peritumoral region includes four annular rings having radii of 3 mm (e.g., a first annular ring extending 0 mm to 3 mm from the tumoral boundary, a second 3 mm to 6 mm annular ring, a third 6 mm to 9 mm annular ring, and a fourth 9 mm to 12 mm annular ring). In another embodiment, the peritumoral region may be defined using other morphological operations on the tumoral boundary, or as a function of a property of the tumor or tumoral region. Defining the peritumoral region includes acquiring electronic data, reading from a computer file, receiving a computer file, reading from a computer memory, or other computerized activity that cannot be practically performed in the human mind.

Operations 100 also includes, at 140, extracting a first set of radiomic features from the peritumoral region. In one embodiment, the first set of radiomic features includes five peritumoral radiomic features. In one embodiment, the first set of radiomic features includes: a standard deviation of a peritumoral Laws level-spot feature extracted from a 0 mm-3 mm annular ring; a range of a peritumoral Gabor feature having a frequency of zero and a theta of zero, extracted from a 3 mm-6 mm annular ring; a kurtosis of a peritumoral Gabor feature having a frequency of two and a theta of zero, extracted from a 3 mm-6 mm annular ring; a skewness of a peritumoral Haralick correlation extracted from a 3 mm-6 mm annular ring; and a kurtosis of a peritumoral co-occurrence of local anisotropic gradient entropy inertia feature extracted from a 3 mm-6 mm annular ring. Extracting the first set of radiomic features includes acquiring electronic data, reading from a computer file, receiving a computer file, reading from a computer memory, or other computerized activity that cannot be practically performed in the human mind.

Operations 100 also includes, at 142, providing the first set of radiomic features to a first machine learning classifier. The first machine learning classifier is trained to distinguish HPs from non-responders (non-R). In one embodiment, the first machine learning classifier is a linear discriminant analysis (LDA) classifier trained to distinguish hyperprogressors from non-responders to immunotherapy. Immunotherapy may include, for example, Nivolumab, pembrolizumab, atezioliumab, or other immunotherapy agent. In another embodiment, the first machine learning classifier may be another type of machine learning classifier, including, for example, a quadratic discriminant analysis (QDA) classifier, a random forest classifier, a support vector machine (SVM), or may be a deep learning classifier, including a convolutional neural network (CNN). Providing the first set of radiomic features to the first machine learning classifier includes acquiring electronic data, reading from a computer file, receiving a computer file, reading from a computer memory, or other computerized activity that cannot be practically performed in the human mind.

Operations 100 also includes, at 144, receiving a first probability from the first machine learning classifier that the region of tissue is HP or non-R. In one embodiment, the first probability is within a range of [0, 1]. In this example, a probability of 0 indicates HP, while a probability of 1 indicates non-R. Other classification schemes may be employed. Receiving the first probability includes acquiring electronic data, reading from a computer file, receiving a computer file, reading from a computer memory, or other computerized activity that cannot be practically performed in the human mind.

Operations 100 also includes, at 150, determining if the first probability that the region of tissue is HP or non-R is within a threshold level. In one embodiment, if the first probability is >=0.9, or <=0.1, the first probability is determined to be within the threshold level. If the first probability is >0.1 and <0.9, the first probability is determined to be not within the threshold level. In another embodiment, other threshold levels may be employed. Upon determining that the first probability that the region of tissue is HP or non-R is within the threshold level, operations 100 also includes, at 152, generating a first classification of the region of tissue as HP or non-R based on the first probability. Operations 100 further includes, at 154, displaying the first classification.

Upon determining that the first probability that the region of tissue is HP or non-R is not within the threshold level, operations 100 includes, at 161, extracting a second set of radiomic features from the peritumoral region and the tumoral region. In one embodiment, the second set of radiomic features includes one tumoral radiomic feature and four peritumoral radiomic features. In one embodiment, the second set of radiomic features includes: a kurtosis of a tumoral Laws spot-spot feature; a range of a peritumoral Gabor feature having a frequency of zero and a theta of zero, extracted from a 3 mm-6 mm annular ring; a kurtosis of a peritumoral Laws level-level feature extracted from a 3 mm-6 mm annular ring; a mean of a peritumoral Laws ripple-edge feature extracted from a 3 mm-6 mm annular ring; and a mean of a peritumoral Laws ripple edge feature extracted from a 9 mm-12 mm annular ring. Extracting the second set of radiomic features includes acquiring electronic data, reading from a computer file, receiving a computer file, reading from a computer memory, or other computerized activity that cannot be practically performed in the human mind.

Operations 100 also includes, at 163, providing the second set of radiomic features to a second machine learning classifier. The second machine learning classifier is trained to distinguish HPs from responders (R). In one embodiment, the second machine learning classifier is an LDA classifier trained to distinguish hyperprogressors from responders to immunotherapy. In another embodiment, the second machine learning classifier may be another type of machine learning classifier, including, for example, a QDA classifier, a random forest classifier, SVM classifier, or may be a deep learning classifier, including a CNN. Providing the second set of radiomic features to the second machine learning classifier includes acquiring electronic data, reading from a computer file, receiving a computer file, reading from a computer memory, or other computerized activity that cannot be practically performed in the human mind.

Operations 100 also includes, at 165, receiving a second probability from the second machine learning classifier that the region of tissue is HP or R. In one embodiment, the second probability is within a range of [0, 1]. In this example, a probability of 0 indicates HP, while a probability of 1 indicates R. Receiving the second probability includes acquiring electronic data, reading from a computer file, receiving a computer file, reading from a computer memory, or other computerized activity that cannot be practically performed in the human mind.

Operations 100 also include, at 167, generating a second classification of the region of tissue as HP or R based on the second probability. Generating the second classification includes acquiring electronic data, reading from a computer file, receiving a computer file, reading from a computer memory, or other computerized activity that cannot be practically performed in the human mind.

Operations 100 further includes, at 169, displaying the second classification. Displaying the first classification or the second classification may include displaying the first classification or the second classification on a computer monitor, a smartphone display, a tablet display, or other displays. Displaying the first classification or the second classification may also include printing the first classification or the second classification. Displaying the first classification or the second classification may also include controlling a hyperprogression prediction system, a personalized medicine system, a monitor, or other display, to display operating parameters or characteristics of a machine learning classifier, during both training and testing, or during clinical operation of the machine learning classifier. By displaying the first classification or the second classification or operating parameters or characteristics of the machine learning classifier, example embodiments provide a timely and intuitive way for a human practitioner to classify a region of tissue as a hyperprogressor or likely to experience other patterns of response, thus improving on existing approaches to classifying tissue as a hyperprogressor or likely to experience other patterns of response. Embodiments may further display the image, the first set of radiomic features, the second set of radiomic features, the first probability, or the second probability.

Figure 9:
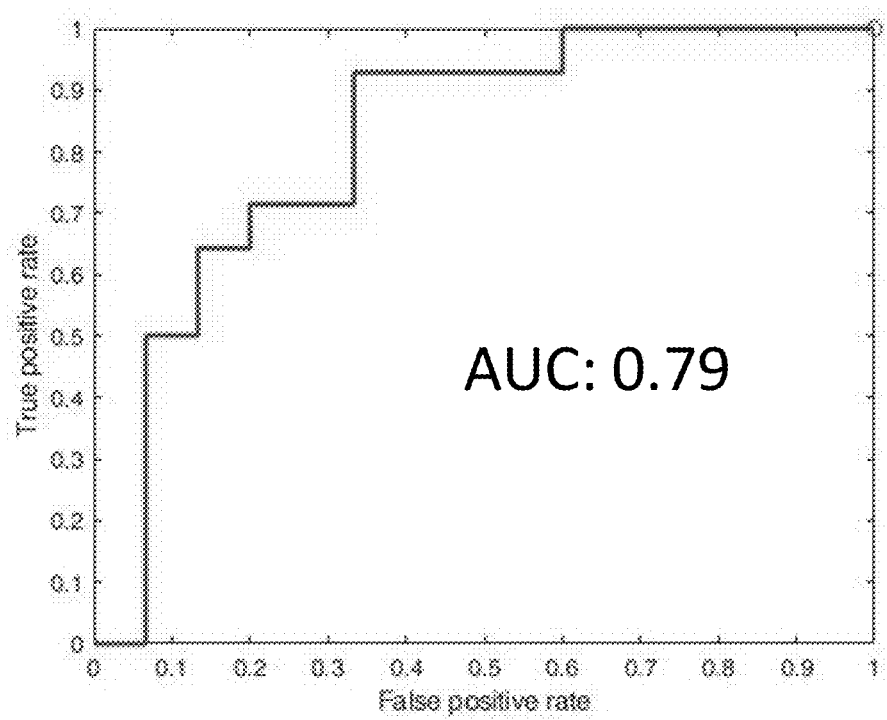
FIG. 9 illustrates area under the receiver operating characteristic curves (AUC) for embodiments.
Figure 9:
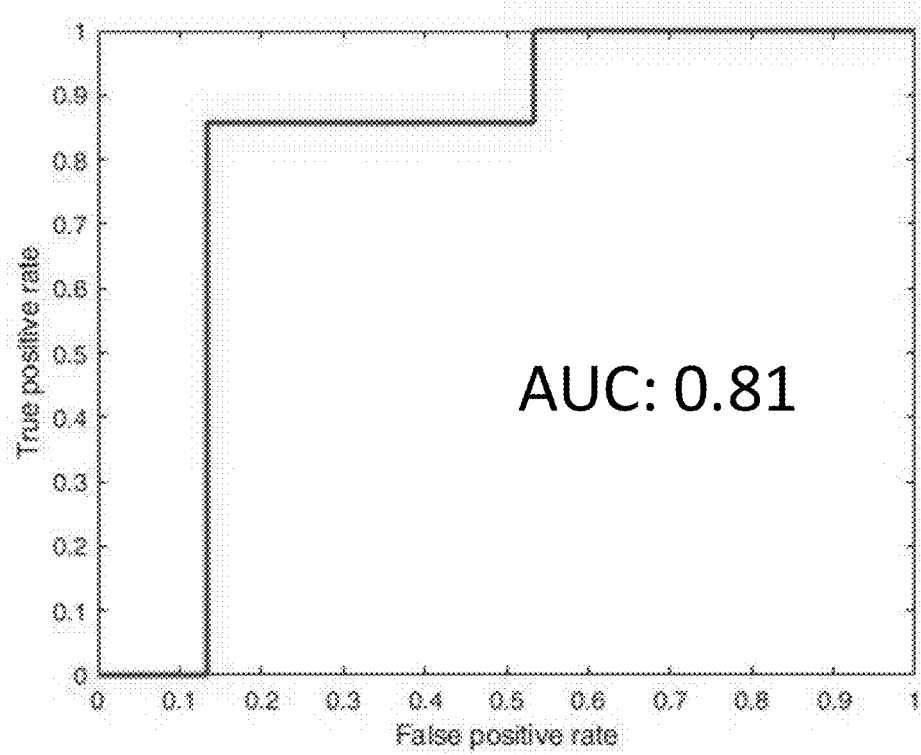

Embodiments provide a highly statistically significant separation between patients who are hyperprogressors and patients who exhibit other patterns of response to immunotherapy, including response or non-response. FIG. 9 illustrates area under the receiver operating characteristic curves (AUC) for embodiments. Embodiments distinguish hyperprogressors from responders with an AUC of at least 0.79, illustrated at 910, an accuracy of at least 0.7241, a sensitivity of at least 0.7143, and a specificity of at least 0.722. Embodiments distinguish hyperprogressors from non-responders with an AUC of at least 0.81, illustrated at 920, an accuracy of at least 0.7931, a sensitivity of at least 0.8531, and a specificity of at least 0.7333. Embodiments thus provide the technical effect of providing improved accuracy in systems, apparatus, processors, computers, or other implementations that distinguish hyperprogressors from patients that will experience other patterns of response.

Figure 2:
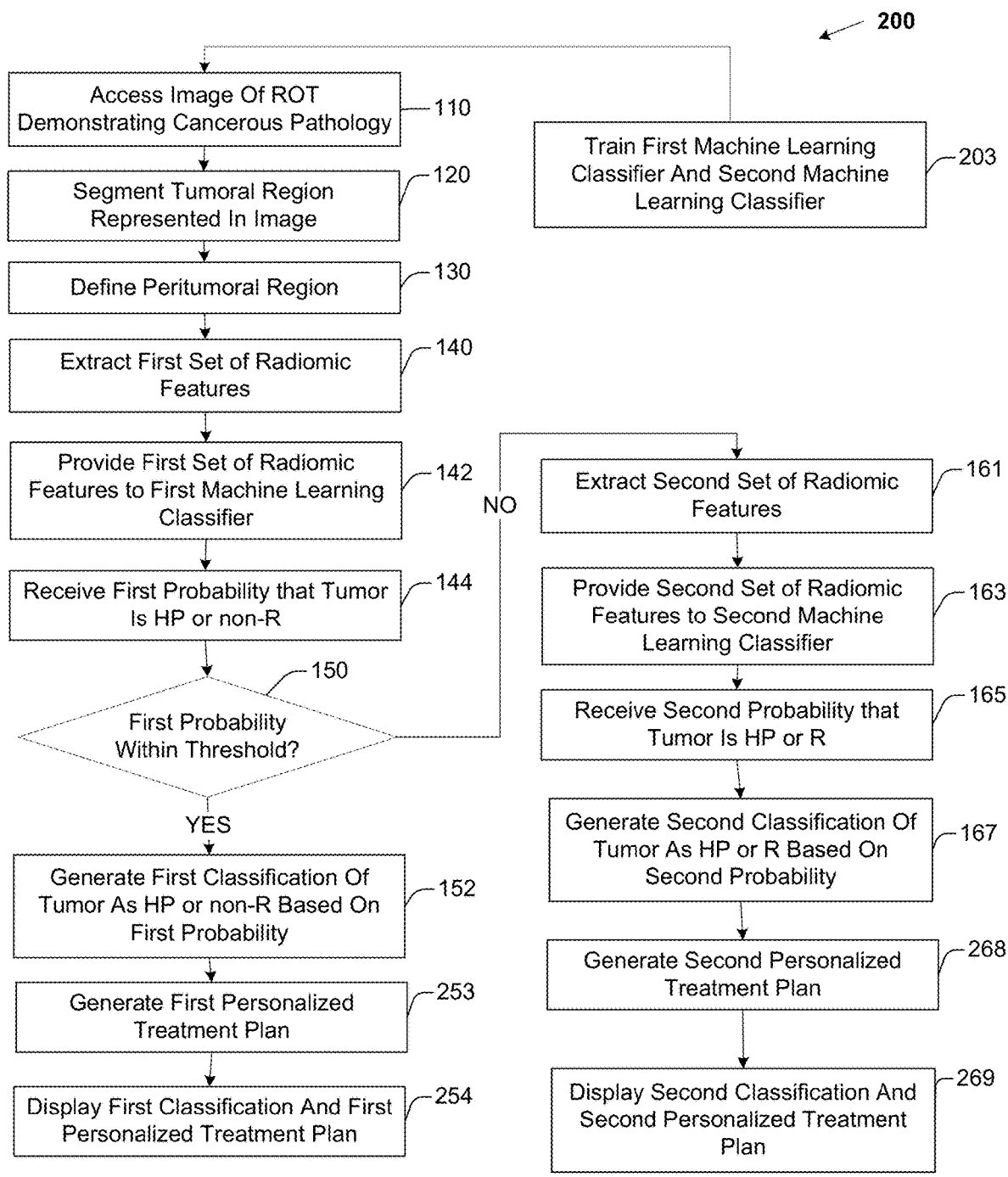
FIG. 2 illustrates a flow diagram of example operations for distinguishing patients who will experience hyperprogression from those who will respond or not respond to immunotherapy.

FIG. 2 illustrates a set of operations 200 that is similar to operations 100 but that includes additional details and elements. Operations 200 include, at 203, training the first machine learning classifier or the second machine learning classifier. In this embodiment, the first machine learning classifier or the second machine learning classifier is trained and tested using a training set of images and a testing set of images. Training the first machine learning classifier or the second machine learning classifier may include training the first machine learning classifier or the second machine learning classifier until a threshold level of accuracy is achieved, until a threshold time has been spent training, until a threshold amount of computational resources have been expended training, or until a user terminates training. Other training termination conditions may be employed. Training the first machine learning classifier or the second machine learning classifier may also include determining which features extracted from a tumoral region or a peritumoral region, or which number of features, is most discriminative in distinguishing a positive class from a negative class (e.g., hyperprogressor, responder or non-responder). In one embodiment, for a first machine learning classifier, supervised learning techniques may be employed. In another embodiment, for second, different machine learning classifier, unsupervised learning techniques may be employed.

Figure 3:
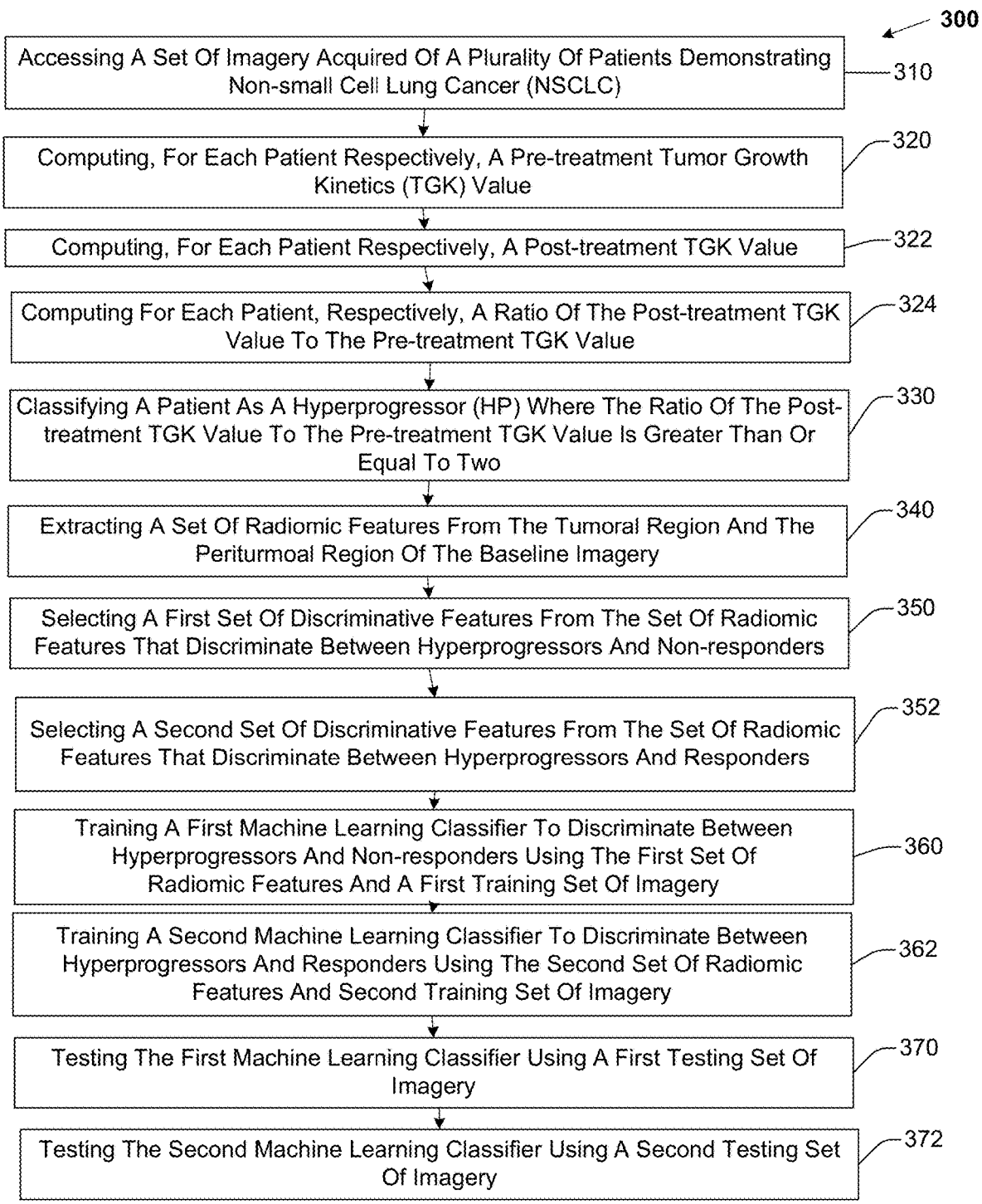
FIG. 3 illustrates a flow diagram of example operations for training a machine learning classifier to distinguish patients who will experience hyperprogression from those who will respond or not respond to immunotherapy.

FIG. 3 illustrates an example set of operations 300 for training a machine learning classifier to differentiate hyperprogression from other response patterns following immunotherapy. Operations 300 includes, at 310, accessing a set of imagery acquired of a plurality of patients demonstrating NSCLC. In this embodiment, each member of the plurality of patients has received three or fewer cycles of immunotherapy treatment and developed progressive NSCLC within three or fewer cycles of immunotherapy treatment. For each patient, the set of imagery includes a pre-baseline image acquired at a first time, a baseline image acquired at a second time later than the first time, and a post-treatment image acquired at a third time later than the second time. The pre-baseline image, the baseline image, and the post-treatment image each include a tumoral region, the tumoral region having a boundary and an area. The pre-baseline image, the baseline image, and the post-treatment image are digitized CT.

Operations 300 also include, at 320, computing, for each patient respectively, a pre-treatment tumor growth kinetics (TGK) value. TGK pre-treatment (e.g., pre-mmunotherapy) may be computed as:

$$TGK_{pre} = \frac{Sum_{baseline} - Sum_{pre\text{-}baseline}}{\text{Time between scans}},$$

where the time between scans is the time between the pre-baseline and baseline scans.

Operations 300 also includes, at 322, computing, for each patient respectively, a post-treatment TGK value. TGK post-treatment (e.g., post-immunotherapy) may be computed as:

$$TGK_{post} = \frac{Sum_{post\text{-}treatment} - Sum_{baseline}}{\text{Time between scans}},$$

where the time between scans is the time between the baseline scan and the post-treatment scan.

Operations 300 also include, at 324, computing for each patient, respectively, a ratio of the post-treatment TGK value to the pre-treatment TGK value.

Operations 300 also includes, at 330, classifying a patient as a hyperprogressor (HP) where the ratio of the post-treatment TGK value to the pre-treatment TGK value is greater than or equal to two. In another embodiment, a patient may be classified as HP where the ratio of the post-treatment TGK value to the pre-treatment TGK value is another, different value (e.g., 1.8, 2.25).

Operations 300 also includes, at 340, extracting a set of radiomic features from the tumoral region and the peritumoral region of the baseline imagery. In one embodiment, the set of radiomic features includes nine-hundred and twenty five (925) radiomic features, including Gabor features, Laws features, Laplace features, and Haralick features. In another embodiment, the set of radiomic features may include other, different features, or another, different number of features.

Operations 300 also includes, at 350, selecting a first set of discriminative features from the set of radiomic features that discriminates between hyperprogressors and non-responders. In one embodiment, the first set of discriminative features is selected using an mRMR feature selection approach. In another embodiment, other feature selection approaches may be employed.

Operations 300 also includes, at 352, selecting a second set of discriminative features from the set of radiomic features that discriminate between hyperprogressors and responders. In one embodiment, the second set of discriminative features is selected using an mRMR feature selection approach. In another embodiment, other feature selection approaches may be employed.

Figure 14:
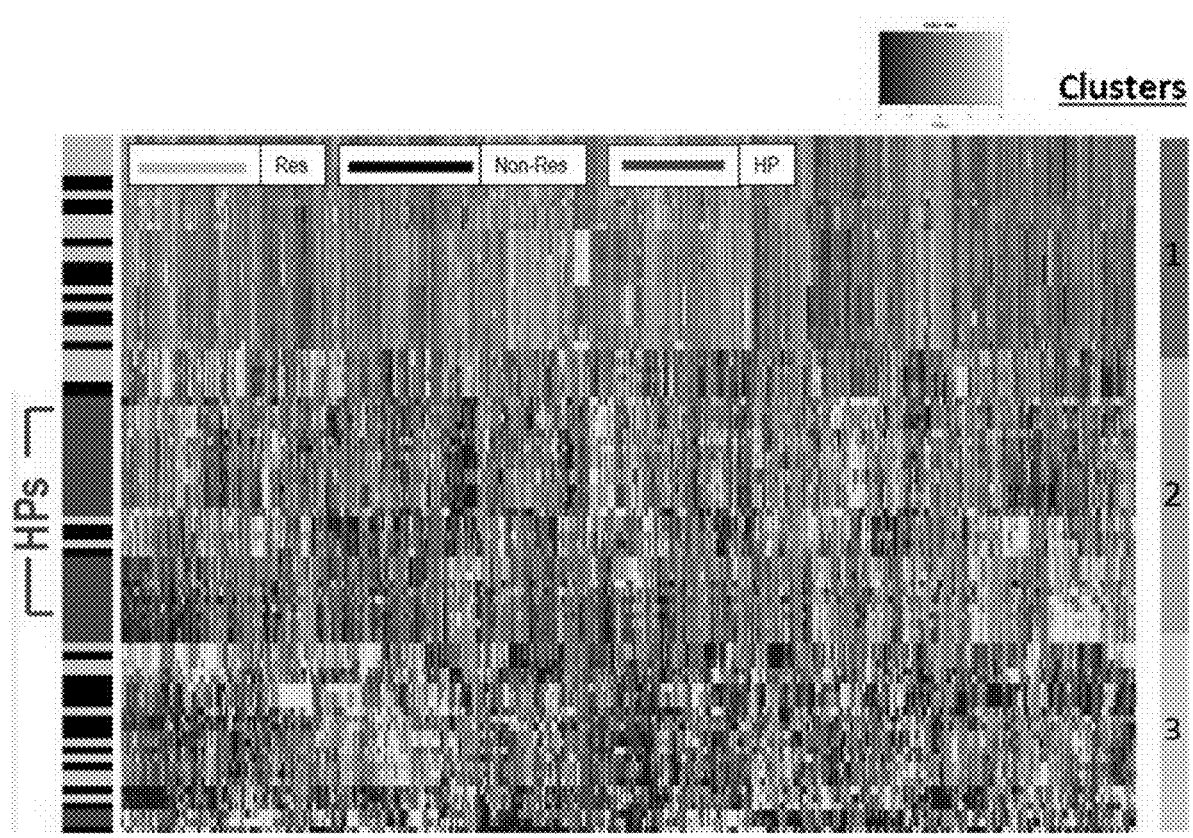
FIG. 14 illustrates a heatmap generated using unsupervised clustering.

FIG. 14 is a heatmap 1410 generated using unsupervised clustering. Heatmap 1410 illustrates uncorrelated features clustered together differentiating HPs from responders and non-responders.

Returning to FIG. 3, operations 300 also includes, at 360, training a first machine learning classifier to discriminate between hyperprogressors and non-responders using the first set of radiomic features and a first training set of imagery. The first training set includes pre-treatment imagery of a patient who experienced hyperprogression, and pre-treatment imagery of a patient who did not respond to immunotherapy.

Operations 300 further includes, at 362, training a second machine learning classifier to discriminate between hyperprogressors and responders using the second set of radiomic features. The second training set includes pre-treatment imagery of a patient who experienced hyperprogression, and pre-treatment imagery of a patient who responded to immunotherapy.

In one embodiment, operations 300 also includes, at 370, testing the first machine learning classifier using a first testing set of imagery. The first testing set includes pre-treatment imagery of a patient who experienced hyperprogression, and pre-treatment imagery of a patient who did not respond to immunotherapy.

In one embodiment, operations 300 further includes, at 372, testing the second machine learning classifier using a second testing set of imagery. The second testing set includes pre-treatment imagery of a patient who experienced hyperprogression, and pre-treatment imagery of a patient who responded to immunotherapy.

Returning to FIG. 2, operations 200 also includes, at 253, generating a first personalized cancer treatment plan. The first personalized cancer treatment play is based on the first classification. Operations 200 also includes, at 254, displaying the first classification and the first personalized cancer treatment plan.

Operations 200 also includes, at 268, generating a second personalized cancer treatment plan. The second personalized cancer treatment plan is based on the second classification. Operations 200 further include, at 269, displaying the second classification and displaying the second personalized cancer treatment plan.

Generating a personalized cancer treatment plan may include computing a first dosage or dosage schedule of a first immunotherapy agent based, at least in part, on the first classification, or a second dosage or dosage schedule of a second, different immunotherapy agent based, at least in part, on the second classification. For example, for region of tissue or patient classified as a hyperprogressor, a first dosage schedule of a first immunotherapy agent may be generated, while for a region of tissue classified as a responder, a second, different dosage schedule of a different immunotherapy agent may be generated. Generating a personalized cancer treatment plan may include generating different follow-up or monitoring schedules depending on the first classification or the second classification. For example, a hyperprogressor may be scheduled, according to the personalized treatment plan, more frequent monitoring, than a responder or non-responder.

While FIGS. 1, 2, and 3, illustrate various actions occurring in serial, it is to be appreciated that various actions illustrated in FIG. 1, 2, or 3, could occur substantially in parallel. By way of illustration, a first process could involve segmenting a tumoral region, a second process could involve extracting a first set of radiomic features, and a third process could involve extracting a second set of radiomic features. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 100, 200, or 300, method 1200, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved prediction of hyperprogression or classification of tissue or patients as likely to experience hyperprogession in NSCLC may produce the technical effect of improving patient outcomes, by more accurately predicting which patients will experience hyperprogression or other patterns of response. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted, when regions of tissue demonstrating NSCLC are more accurately and more quickly analyzed. Controlling an NSCLC hyperprogression prediction apparatus based on improved, non-destructive, more accurate prediction of NSCLC hyperprogression further improves the operation of the system, processor, or apparatus, since the accuracy of the system, processor, or apparatus is increased and unnecessary operations will not be performed. Embodiments described herein, including at least operations 100, 200, or 300, apparatus 400 and 500, or method 1200, resolve features extracted from digitized CT imagery at a higher order or higher level than a human can resolve in the human mind or with pencil and paper. For example, the kurtosis of a Laws ripple-edge feature extracted from a 3 mm-6 mm peritumoral ring is not a property of a region of tissue that a human eye can perceive, nor can its extraction from a digitized image stored in computer memory be practically performed in the human mind. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 4:
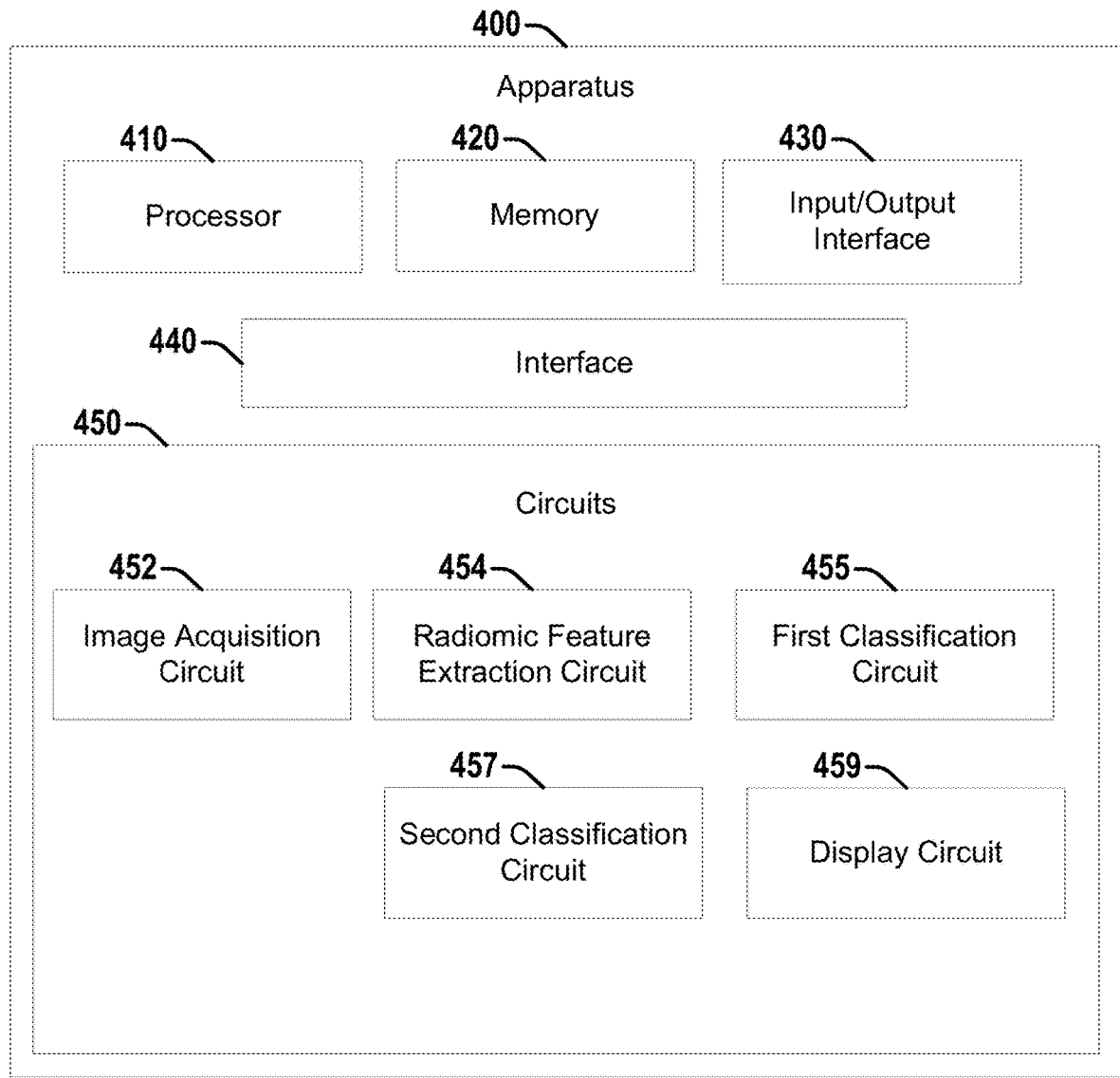
FIG. 4 illustrates an example apparatus configured to distinguish patients who will experience hyperprogression from those who will respond or not respond to immunotherapy.

FIG. 4 illustrates an example apparatus 400. Apparatus 400 may be configured for predicting hyperprogression in NSCLC, or distinguishing patients who are likely to experience hyperprogression from those who are likely to respond to immunotherapy, or not respond to immunotherapy. Apparatus 400 includes a processor 410. Apparatus 400 also includes a memory 420. Processor 410 may, in one embodiment, include circuitry such as, but not limited to, one or more single-core or multi-core processors. Processor 410 may include any combination of general-purpose processors and dedicated processors (e.g., graphics processors, application processors, etc.). The processors may be coupled with or may include memory (e.g. memory 420) or storage and may be configured to execute instructions stored in the memory 420 or storage to enable various apparatus, applications, or operating systems to perform the operations. Memory 420 is configured to store a digitized image of a region of tissue demonstrating cancerous pathology. The digitized image has a plurality of pixels, a pixel having an intensity. Memory 420 may be further configured to store a training set that includes a plurality of digitized images of regions of tissue that demonstrate cancerous pathology, where a first member of the training set includes an image of a region of tissue that experienced hyperprogression, and a second, different member of the training set includes an image of a region of tissue that did or did not respond to immunotherapy. Memory 420 may be further configured to store a testing set that includes a plurality of digitized images of regions of tissue that demonstrate cancerous pathology, where a first member of the training set includes an image of a region of tissue that experienced hyperprogression, and a second, different member of the training set includes a region of tissue that did or did not respond to immunotherapy.

Apparatus 400 also includes an input/output (I/O) interface 430, a set of circuits 450, and an interface 440 that connects the processor 410, the memory 420, the I/O interface 430, and the set of circuits 450. I/O interface 430 may be configured to transfer data between memory 420, processor 410, circuits 450, and external devices, for example, a NSCLC hyperprogression prediction system or a CT system.

The set of circuits 450 includes an image acquisition circuit 452, a radiomic feature extraction circuit 454, a first classification circuit 455, a second classification circuit 457, and a display circuit 459.

Image acquisition circuit 452 is configured to access an image of a region of tissue demonstrating cancerous pathology. The region of tissue includes a tumor region. The image has a plurality of pixels, a pixel having an intensity. Accessing the image may include accessing a digitized image stored in memory 420. In one embodiment, the digitized image is a digitized CT image of tissue demonstrating NSCLC. In another embodiment, other imaging modalities (e.g., MRI), or imaging parameters may be employed. In one embodiment, accessing the image may include accessing a digitized image stored in a data storage device, including a hard disk drive, a solid state device, a tape drive, or accessing a digitized image over a local area network. Accessing the digitized image includes acquiring electronic data, reading from a computer file, receiving a computer file, reading from a computer memory, or other computerized activity that cannot be practically performed in a human mind.

Image acquisition circuit 452 is also configured to define a tumoral boundary by segmenting the tumoral region represented in the image. In one embodiment, the tumoral region is segmented using a watershed approach. In another embodiment, other segmentation approaches, including deep-learning techniques, may be employed.

Image acquisition circuit 452 is also configured to define a peritumoral region based on the tumoral boundary, where the peritumoral region includes a plurality of annular rings. Image acquisition circuit 452 may be configured to define the peritumoral region by dilating the tumoral boundary as described herein. In another embodiment, image acquisition circuit 452 may be configured to define the peritumoral region using another, different technique. For example, a centroid of the tumoral region may be computed, and image acquisition circuit 452 may generate a series of concentric circular or spherical regions to a threshold diameter from the centroid.

Radiomic feature extraction circuit 454 is configured to extract a first set of radiomic features from the peritumoral region. Radiomic feature extraction circuit 454 is also configured to extract a second set of radiomic features from the peritumoral region and the tumoral region.

In one embodiment, the first set of radiomic features includes: a standard deviation of a peritumoral Laws level-spot feature extracted from a 0 mm-3 mm annular ring; a range of a peritumoral Gabor feature having a frequency of zero and a theta of zero, extracted from a 3 mm-6 mm annular ring; a kurtosis of a peritumoral Gabor feature having a frequency of two and a theta of zero, extracted from a 3 mm-6 mm annular ring; a skewness of a peritumoral Haralick correlation extracted from a 3 mm-6 mm annular ring; and a kurtosis of a peritumoral co-occurrence of local anisotropic gradient entropy inertia feature extracted from a 3 mm-6 mm annular ring.

In one embodiment, the second set of radiomic features includes: a kurtosis of a tumoral Laws spot-spot feature; a range of a peritumoral Gabor feature having a frequency of zero and a theta of zero, extracted from a 3 mm-6 mm annular ring; a kurtosis of a peritumoral Laws level-level feature extracted from a 3 mm-6 mm annular ring; a mean of a peritumoral Laws ripple-edge feature extracted from a 3 mm-6 mm annular ring; and a mean of a peritumoral Laws ripple edge feature extracted from a 9 mm-12 mm annular ring. In another embodiment, the first set of radiomic features or the second set of radiomic features may include other, different radiomic features, or another, different number of radiomic features.

First classification circuit 455 is configured to compute a first probability, based on the first set of radiomic features, that the region of tissue is a hyperprogressor (HP) or non-responder (non-R) to immunotherapy. First classification circuit 455 is also configured to generate a first classification of the region of tissue as HP or non-R based on the first probability. In one embodiment, first classification circuit 455 is configured as an LDA classifier, and computes the first probability using an LDA classification approach. In another embodiment, first classification circuit 455 may be configured as another, different type of machine learning or deep learning classifier. For example, first classification circuit 455 may be configured to use a QDA classification approach, a random forests classification approach, a SVM classification approach, or a CNN classification approach.

Second classification circuit 457 is configured to determine if the first probability that the region of tissue is HP or non-R is not within a threshold level. Second classification circuit 457 is also configured to, upon determining that the first probability that the region of tissue is HP or non-R is not within a threshold level, compute a second probability, based on the second set of radiomic features, that the region of tissue is a HP or responder (R) to immunotherapy. Second classification circuit 457 is also configured to generate a second classification of the region of tissue as HP or R based on the second probability. In one embodiment, second classification circuit 457 is configured as an LDA classifier, and computes the second probability using an LDA classification approach. In another embodiment, second classification circuit 457 may be configured as another, different type of machine learning or deep learning classifier. For example, second classification circuit 457 may be configured to use a QDA classification approach, a random forests classification approach, a SVM classification approach, or a CNN classification approach.

Display circuit 459 is configured to display the first classification or the second classification, and the image. Display circuit 459 may display the first classification or the second classification, and the image, on a computer monitor, a smartphone display, a tablet display, or other displays. In one embodiment, display circuit 459 is further configured to display at least one of the first probability, the second probability, the tumoral region, the peritumoral region, the first set of radiomic features, or the second set of radiomic features. Displaying the first classification or the second classification, the image, and at least one of the first probability, the second probability, the tumoral region, the peritumoral region, the first set of radiomic features, or the second set of radiomic features may also include printing the first classification or the second classification, the image, and at least one of the first probability, the second probability, the tumoral region, the peritumoral region, the first set of radiomic features, or the second set of radiomic features.

Figure 5:
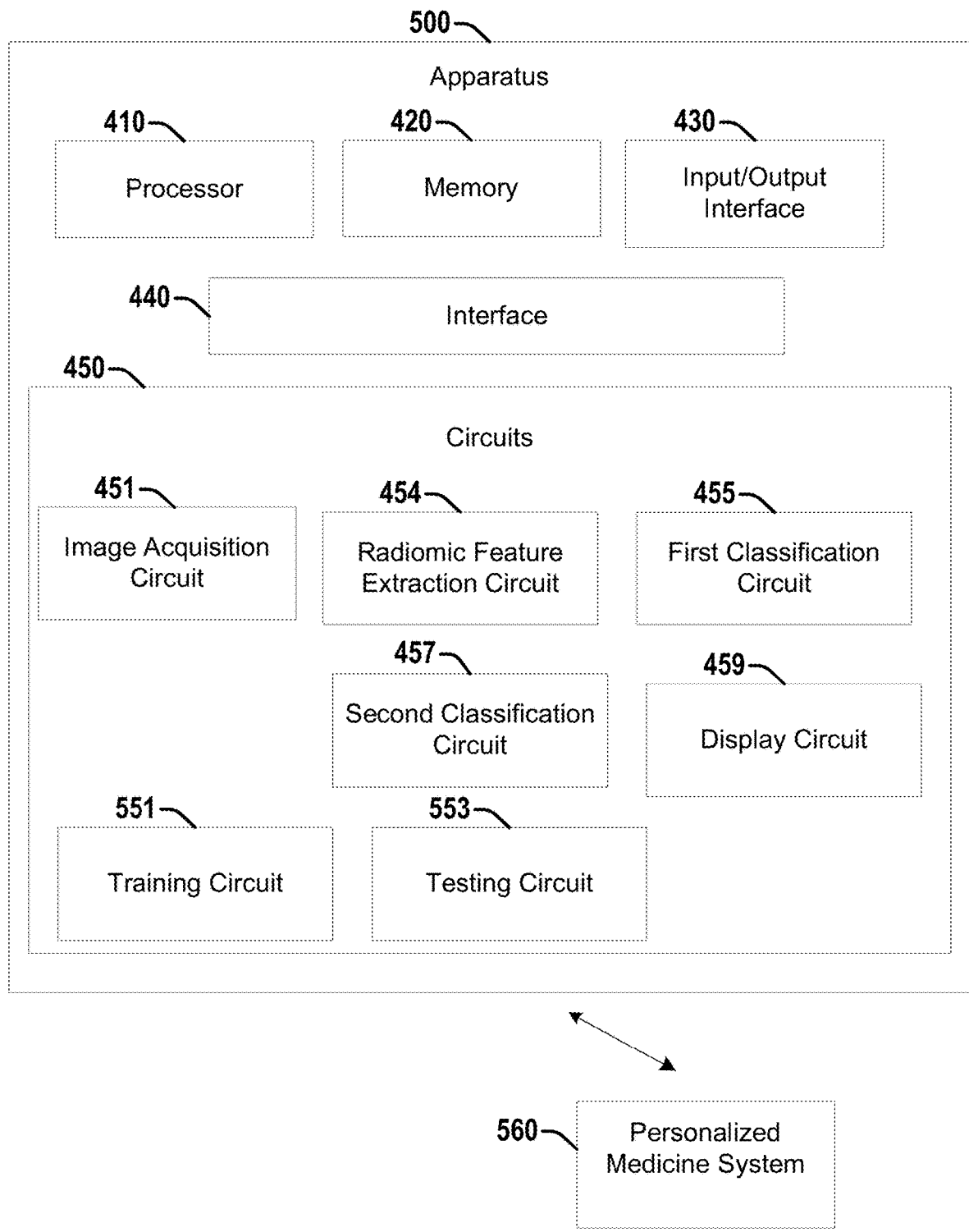
FIG. 5 illustrates an example apparatus configured to distinguish patients who will experience hyperprogression from those who will respond or not respond to immunotherapy.

Embodiments may include a training circuit. FIG. 5 illustrates an example apparatus 500 that is similar to apparatus 400 but that includes additional elements and details. Apparatus 500 includes a training circuit 551 and a testing circuit 553. Training circuit 551 may be configured to train first classification circuit 455, second classification circuit 457, or other machine learning classifier, to classify an image, including a CT image of a region of tissue demonstrating NSCLC, according to techniques described herein.

In one embodiment, training circuit 551 is configured to access a set of imagery acquired of a plurality of patients demonstrating NSCLC, where each patient has received three or fewer cycles of immunotherapy treatment and developed progressive NSCLC within the three or fewer cycles of immunotherapy treatment. For each patient, the set of imagery includes a pre-baseline image acquired at a first time, a baseline image acquired at a second time later than the first time, and a post-treatment image acquired at a third time later than the second time. The pre-baseline image, the baseline image, and the post-treatment image each include a tumoral region and a peritumoral region, the tumoral region having a boundary and an area.

Training circuit 551 is also configured to compute, for each patient respectively, a pre-treatment tumor growth kinetics (TGK) value. Training circuit 551 is also configured to compute, for each patient respectively, a post-treatment TGK value. Training circuit 551 is also configured to compute for each patient, respectively, a ratio of the post-treatment TGK value to the pre-treatment TGK value. Training circuit 551 is also configured to classify a patient as HP where the ratio of the post-treatment TGK value to the pre-treatment TGK value is greater than or equal to two. In another embodiment, training circuit 551 may be configured to classify a patient or region of tissue as HP based on other, different criteria.

Training circuit 551 is also configured to extract a set of radiomic features from the tumoral region and the peritumoral region of the baseline imagery. Training circuit 551 is also configured to select, using an mRMR feature selection approach, a first set of discriminative radiomic features from the set of radiomic features that discriminate between hyperprogressors and non-responders. Training circuit 551 is also configured to select, using an mRMR feature selection approach, a second set of discriminative radiomic features from the set of radiomic features that discriminate between hyperprogressors and responders. In one embodiment, the first set of discriminative radiomic features and the second set of discriminative radiomic features include five radiomic features each.

Training circuit 551 is also configured to train the first classification circuit 455 to discriminate between hyperprogressors and non-responders using the first set of radiomic features and a first training set of imagery. The first training set includes pre-treatment imagery of a patient who experienced hyperprogression, and pre-treatment imagery of a patient who did not respond to immunotherapy. Training circuit 551 is also configured to train the second classification circuit 457 to discriminate between hyperprogressors and responders using the second set of radiomic features and second training set of imagery. The second training set includes pre-treatment imagery of a patient who experienced hyperprogression, and pre-treatment imagery of a patient who responded to immunotherapy.

Training first classification circuit 455 or second classification circuit 457 may include training first classification circuit 455 or second classification circuit 457 until a threshold level of accuracy is achieved, until a threshold time has been spent training first classification circuit 455 or second classification circuit 457, until a threshold amount of computational resources have been expended training first classification circuit 455 or second classification circuit 457, or until a user terminates training. Other training termination conditions may be employed. Training circuit 551 may also be configured to determine which features extracted from a tumoral region or peritumoral region, or which number of features, is most discriminative in distinguishing a positive class from a negative class (e.g., hyperprogressor, responder, non-responder).

Testing circuit 553 is configured to test first classification circuit 455 to discriminate between patients who experienced hyperprogression and patients who did not respond to immunotherapy using a first testing set of imagery. The first testing set includes pre-treatment imagery of a patient who experienced hyperprogression, and pre-treatment imagery of a patient who did not respond to immunotherapy. Testing circuit 553 is also configured to test second classification circuit 457 to discriminate between patients who experienced hyperprogression and patients who responded to immunotherapy using a second testing set of imagery. The second testing set includes pre-treatment imagery of a patient who experienced hyperprogression, and pre-treatment imagery of a patient who responded to immunotherapy.

FIG. 5 further illustrates personalized medicine system 560. Apparatus 500 may be configured to transmit the first classification, the second classification, the image, or other information to personalized medicine system 560. Apparatus 500 may be configured to control personalized medicine system 560 to display at least one of the image, the first classification, the second classification, the first set of radiomic features, the second set of radiomic features, the first probability, the second probability, or a personalized cancer treatment plan. In one embodiment, personalized medicine system 560 may be configured as a member of circuits 550. Personalized medicine system 560 may be configured to generate a personalized NSCLC treatment plan based, at least in part, on the first classification or the second classification. For example, personalized medicine system 560 may be configured to compute a first dosage or dosage schedule of a first immunotherapy agent based, at least in part, on the first classification, or a second dosage or dosage schedule of a second, different immunotherapy agent based, at least in part, on the second classification. For example, for region of tissue classified as a hyperprogressor, a first dosage schedule may be generated, while for a region of tissue classified as a responder, a second, different dosage schedule of a different immunotherapy agent may be generated. Different personalized NSCLC treatment plans may also generate different follow-up or monitoring schedules depending on the first classification or the second classification. For example, a hyperprogressor may be scheduled, according to the personalized NSCLC treatment plan, more frequent monitoring, than a responder or non-responder.

Figure 6:
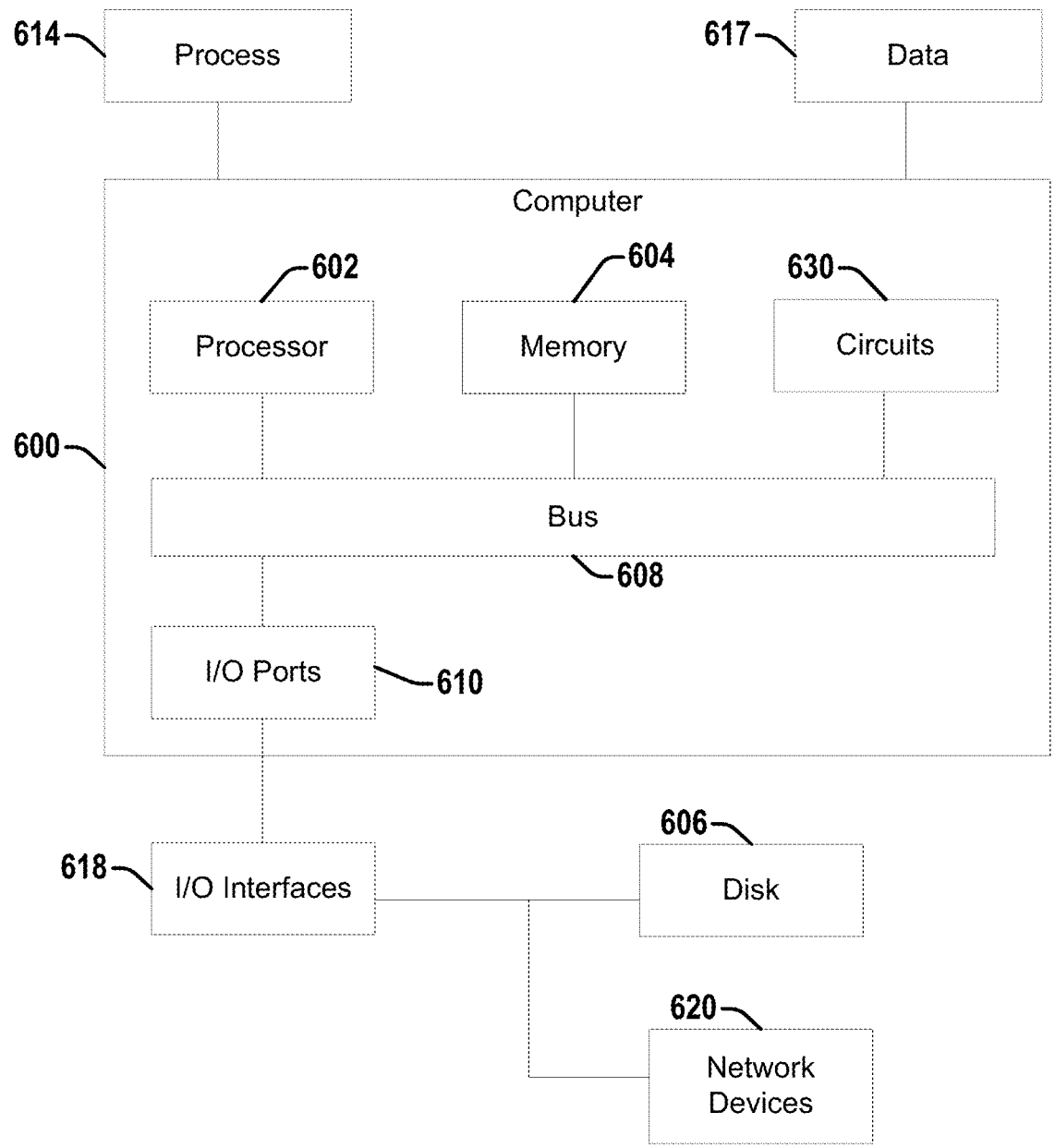
FIG. 6 illustrates an example computer in which embodiments described herein may operate.

FIG. 6 illustrates an example computer 600 in which example methods illustrated herein can operate and in which example methods, apparatus, circuits, operations, or logics may be implemented. In different examples, computer 600 may be part of a NSCLC hyperprogression prediction system or apparatus, a CT system, or MRI system, may be operably connectable to a NSCLC hyperprogression prediction system or apparatus, or a CT system or MRI system.

Computer 600 includes a processor 602, a memory 604, and input/output (I/O) ports 610 operably connected by a bus 608. In one example, computer 600 may include a set of logics or circuits 630 that perform operations for, or a method of, predicting hyperprogression or of distinguishing hyperprogressors from responders or non-responders to immunotherapy in NSCLC using a machine learning classifier. Thus, the set of circuits 630, whether implemented in computer 600 as hardware, firmware, software, and/or a combination thereof may provide means (e.g., hardware, firmware, circuits) for predicting hyperprogression or distinguishing hyperprogressors from responders or non-responders to immunotherapy in NSCLC. In different examples, the set of circuits 630 may be permanently and/or removably attached to computer 600.

Processor 602 can be a variety of various processors including dual microprocessor and other multi-processor architectures. Processor 602 may be configured to perform operations or steps of methods claimed and described herein. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, or a memory stick. Furthermore, disk 606 may include optical drives like a CD-ROM or a digital video ROM drive (DVD ROM). Memory 604 can store processes 614 or data 617, for example. Data 617 may, in one embodiment, include digitized CT imagery. Disk 606 or memory 604 can store an operating system that controls and allocates resources of computer 600.

Bus 608 can be a single internal bus interconnect architecture or other bus or mesh architectures. While a single bus is illustrated, it is to be appreciated that computer 600 may communicate with various devices, circuits, logics, and peripherals using other buses that are not illustrated (e.g., PCIE, SATA, Infiniband, 794, USB, Ethernet).

Computer 600 may interact with input/output devices via I/O interfaces 618 and input/output ports 610. Input/output devices can include, but are not limited to, CT systems, MRI systems, digital whole slide scanners, an optical microscope, a keyboard, a microphone, a pointing and selection device, cameras, video cards, displays, disk 606, network devices 620, or other devices. Input/output ports 610 can include but are not limited to, serial ports, parallel ports, or USB ports.

Computer 600 may operate in a network environment and thus may be connected to network devices 620 via I/O interfaces 618 or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), or other networks, including the cloud.

Figure 12:
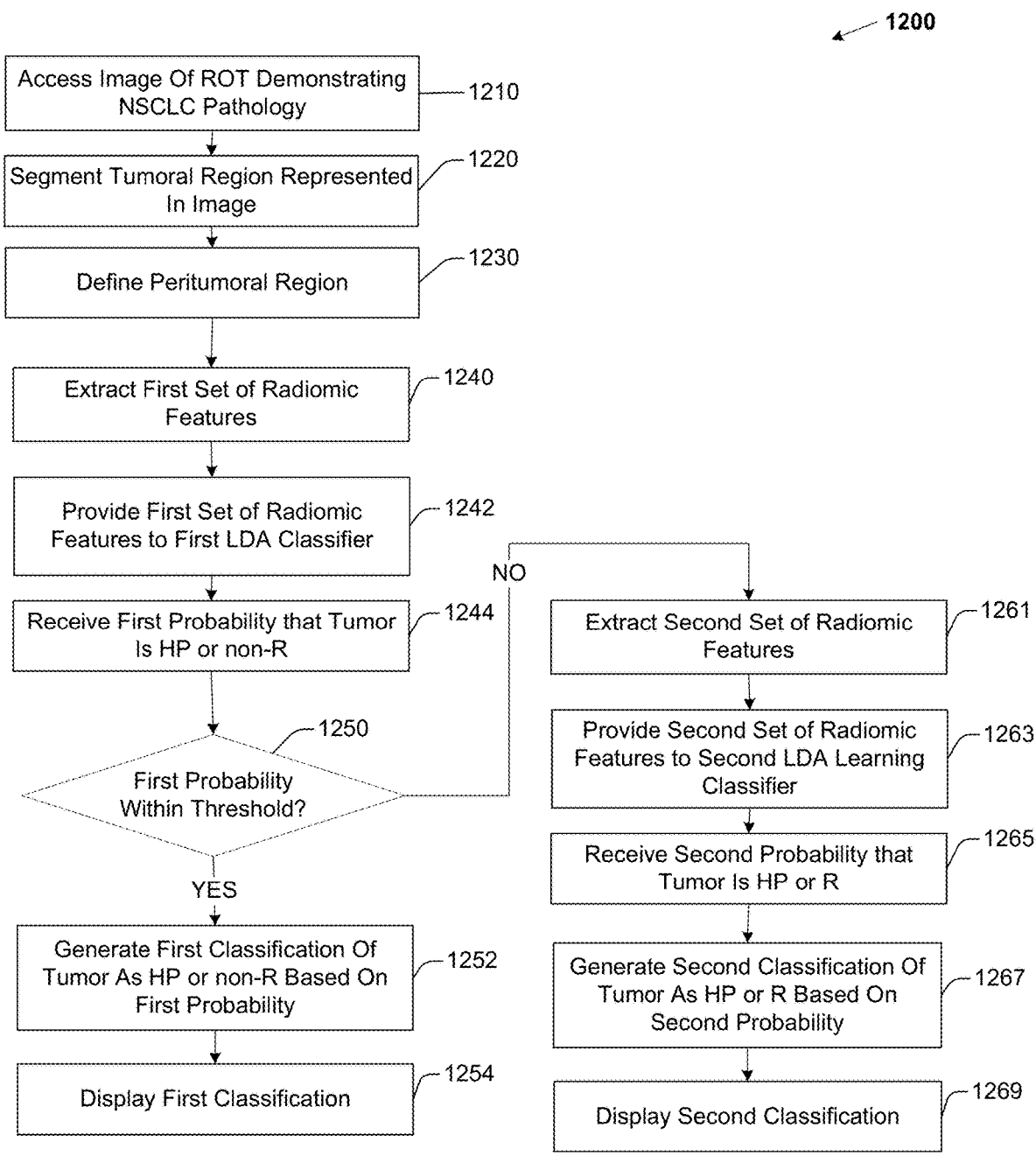
FIG. 12 illustrates an example method for distinguishing patients who will experience hyperprogression from those who will respond or not respond to immunotherapy.

FIG. 12 illustrates an example method 1200. Method 1200 includes, at 1210 accessing a digitized pre-immunotherapy treatment CT image of a region of tissue demonstrating NSCLC pathology. The image includes a plurality of pixels, a pixel having an intensity. Accessing the digitized pre-immunotherapy CT image includes acquiring electronic data, reading from a computer file, receiving a computer file, reading from a computer memory, or other computerized activity that cannot be practically performed in the human mind.

Method 1200 also includes, at 1220 defining a tumoral boundary by segmenting a tumoral region represented in the image. In one embodiment, defining the tumoral boundary by segmenting the tumoral region represented in the image includes automatically segmenting the tumoral region using a watershed approach. In another embodiment, other automated techniques may be employed to segment the tumoral region, including deep learning approaches. Defining the tumoral boundary image includes acquiring electronic data, reading from a computer file, receiving a computer file, reading from a computer memory, or other computerized activity that cannot be practically performed in the human mind.

Method 1200 also includes, at 1230, defining a peritumoral region based on a morphological dilation of the tumoral boundary. The peritumoral region includes a plurality of annular rings. Defining the peritumoral region image includes acquiring electronic data, reading from a computer file, receiving a computer file, reading from a computer memory, or other computerized activity that cannot be practically performed in the human mind.

Method 1200 also includes, at 1240, extracting a first set of radiomic features from the peritumoral region. In one embodiment, the first set of radiomic features includes five peritumoral radiomic features. Extracting the first set of radiomic features image includes acquiring electronic data, reading from a computer file, receiving a computer file, reading from a computer memory, or other computerized activity that cannot be practically performed in the human mind.

Method 1200 also includes, at 1242, providing the first set of radiomic features to a first LDA classifier trained to distinguish hyperprogressors (HP) from non-responders (non-R). Providing the first set of radiomic features to the first LDA classifier image includes acquiring electronic data, reading from a computer file, receiving a computer file, reading from a computer memory, or other computerized activity that cannot be practically performed in the human mind.

Method 1200 also includes, at 1244, receiving a first probability from the first LDA classifier that the region of tissue is HP or non-R. Receiving the first probability image includes acquiring electronic data, reading from a computer file, receiving a computer file, reading from a computer memory, or other computerized activity that cannot be practically performed in the human mind.

Method 1200 also includes, at 1250, determining if the first probability that the region of tissue is HP or non-R is within a threshold level. Upon determining that the first probability that the region of tissue is HP or non-R is within a threshold level, method 1200 also includes, at 1252, generating a first classification of the region of tissue as HP or non-R based on the first probability, and at 1254, displaying the first classification.

Upon determining that the first probability that the region of tissue is HP or non-R is not within the threshold level, method 1200 includes, at 1261, extracting a second set of radiomic features from the tumoral region and the peritumoral region. In one embodiment, the second set of radiomic features includes four peritumoral radiomic features and one tumoral radiomic feature. Extracting the second set of radiomic features image includes acquiring electronic data, reading from a computer file, receiving a computer file, reading from a computer memory, or other computerized activity that cannot be practically performed in the human mind.

Method 1200 also includes, at 1263, providing the second set of radiomic features to a second LDA classifier trained to distinguish HPs from responders (R). Providing the second set of features to the second LDA classifier image includes acquiring electronic data, reading from a computer file, receiving a computer file, reading from a computer memory, or other computerized activity that cannot be practically performed in the human mind.

Method 1200 also includes, at 1265, receiving a second probability from the second LDA classifier that the region of tissue is HP or R. Receiving the second probability image includes acquiring electronic data, reading from a computer file, receiving a computer file, reading from a computer memory, or other computerized activity that cannot be practically performed in the human mind.

Method 1200 also includes, at 1267, generating a second classification of the region of tissue as HP or R based on the second probability. Generating the second classification image includes acquiring electronic data, reading from a computer file, receiving a computer file, reading from a computer memory, or other computerized activity that cannot be practically performed in the human mind.

Method 1200 further includes, at 1269, displaying the second classification. Displaying the first classification or the second classification may include displaying the first classification or the second classification on a computer monitor, a smartphone display, a tablet display, or other displays. In one embodiment, displaying the first classification or the second classification further includes displaying at least one of the image, the first set of radiomic features, the second set of radiomic features, the first probability, or the second probability.

In one embodiment, method 1200 further includes generating a personalized NSCLC treatment plan based on the first classification or the second classification. In this embodiment, method 1200 also includes displaying the personalized NSCLC treatment plan.

Examples herein can include subject matter such as an apparatus, an NSCLC hyperprogression prediction system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting hyperprogression in NSCLC or distinguishing patients who will experience hyperprogression from other patterns of response to immunotherapy, including response or non-response, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:
   accessing a pre-immunotherapy treatment image of a region of tissue demonstrating cancerous pathology, the image including a plurality of pixels, a pixel having an intensity;
   defining a tumoral boundary by segmenting a tumoral region represented in the image;
   defining a peritumoral region based on the tumoral boundary, where the peritumoral region includes a plurality of annular rings;
   extracting a first set of radiomic features from the peritumoral region;
   providing the first set of radiomic features to a first machine learning classifier trained to distinguish hyper-progressors (HP) from non-responders (non-R);
   receiving a first probability from the first machine learning classifier that the region of tissue is HP or non-R;
   upon determining that the first probability that the region of tissue is HP or non-R is within a threshold level:
      generating a first classification of the region of tissue as HP or non-R based on the first probability; and
      displaying the first classification;
   upon determining that the first probability that the region of tissue is HP or non-R is not within the threshold level:
      extracting a second set of radiomic features from the peritumoral region and the tumoral region;
      providing the second set of radiomic features to a second machine learning classifier trained to distinguish HPs from responders (R);
      receiving a second probability from the second machine learning classifier that the region of tissue is HP or R;
      generating a second classification of the region of tissue as HP or R based on the second probability; and
      displaying the second classification.

2. The non-transitory computer-readable storage device of claim 1, where the first set of radiomic features includes five peritumoral radiomic features.

3. The non-transitory computer-readable storage device of claim 2, where the first set of radiomic features includes:
   a standard deviation of a peritumoral Laws level-spot feature extracted from a 0 mm-3 mm annular ring;
   a range of a peritumoral Gabor feature having a frequency of zero and a theta of zero, extracted from a 3 mm-6 mm annular ring;
   a kurtosis of a peritumoral Gabor feature having a frequency of two and a theta of zero, extracted from a 3 mm-6 mm annular ring;
   a skewness of a peritumoral Haralick correlation extracted from a 3 mm-6 mm annular ring; and
   a kurtosis of a peritumoral co-occurrence of local anisotropic gradient entropy inertia feature extracted from a 3 mm-6 mm annular ring.

4. The non-transitory computer-readable storage device of claim 1, where the second set of radiomic features includes one tumoral radiomic feature and four peritumoral radiomic features.

5. The non-transitory computer-readable storage device of claim 4, where the second set of radiomic features includes:
   a kurtosis of a tumoral Laws spot-spot feature;
   a range of a peritumoral Gabor feature having a frequency of zero and a theta of zero, extracted from a 3 mm-6 mm annular ring;
   a kurtosis of a peritumoral Laws level-level feature extracted from a 3 mm-6 mm annular ring;
   a mean of a peritumoral Laws ripple-edge feature extracted from a 3 mm-6 mm annular ring; and
   a mean of a peritumoral Laws ripple edge feature extracted from a 9 mm-12 mm annular ring.

6. The non-transitory computer-readable storage device of claim 1, where the image is a pre-immunotherapy treatment digitized computed tomography (CT) image of a region of tissue demonstrating non-small cell lung cancer (NSCLC).

7. The non-transitory computer-readable storage device of claim 1, where defining the tumoral boundary by segmenting the tumoral region represented in the image includes automatically segmenting the tumoral region using a watershed approach.

8. The non-transitory computer-readable storage device of claim 1, where defining the peritumoral region based on the tumoral boundary includes dilating the tumoral boundary a threshold distance.

9. The non-transitory computer-readable storage device of claim 1, where the first machine learning classifier is a linear discriminant analysis (LDA) classifier trained to distinguish hyperprogressors from non-responders to immunotherapy.

10. The non-transitory computer-readable storage device of claim 1, where the second machine learning classifier is a linear discriminant analysis (LDA) classifier trained to distinguish hyperprogressors from responders to immunotherapy.

11. The non-transitory computer-readable storage device of claim 1, the operations further comprising training the first machine learning classifier or the second machine learning classifier.

12. The non-transitory computer-readable storage device of claim 11, where training the first machine learning classifier or the second machine learning classifier includes controlling the processor to perform operations comprising:
accessing a set of imagery acquired of a plurality of patients demonstrating non-small cell lung cancer (NSCLC), where each patient has received three or fewer cycles of immunotherapy treatment and developed progressive NSCLC within three or fewer cycles of immunotherapy treatment, where for each patient, the set of imagery includes a pre-baseline image acquired at a first time, a baseline image acquired at a second time later than the first time, and a post-treatment image acquired at a third time later than the second time, where the pre-baseline image, the baseline image, and the post-treatment image each include a tumoral region and a peritumoral region, the tumoral region having a boundary and an area;
computing, for each patient respectively, a pre-treatment tumor growth kinetics (TGK) value;
computing, for each patient respectively, a post-treatment TGK value;
computing for each patient, respectively, a ratio of the post-treatment TGK value to the pre-treatment TGK value;
classifying a patient as a hyperprogressor (HP) where the ratio of the post-treatment TGK value to the pre-treatment TGK value is greater than or equal to two;
extracting a set of radiomic features from the tumoral region and the peritumoral region of the baseline imagery;
selecting a first set of discriminative features from the set of radiomic features that discriminate between hyperprogressors and non-responders;
selecting a second set of discriminative features from the set of radiomic features that discriminate between hyperprogressors and responders;
training the first machine learning classifier to discriminate between hyperprogressors and non-responders using the first set of radiomic features and a first training set of imagery, where the first training set includes pre-treatment imagery of a patient who experienced hyperprogression, and pre-treatment imagery of a patient who did not respond to immunotherapy; and
training the second machine learning classifier to discriminate between hyperprogressors and responders using the second set of radiomic features and second training set of imagery, where the second training set includes pre-treatment imagery of a patient who experienced hyperprogression, and pre-treatment imagery of a patient who responded to immunotherapy.

13. The non-transitory computer-readable storage device of claim 12, where training the first machine learning classifier or the second machine learning classifier further comprises controlling the processor to perform operations comprising:
testing the first machine learning classifier to discriminate between patients who experienced hyperprogression and patients who did not respond to immunotherapy using a first testing set of imagery, where the first testing set includes pre-treatment imagery of a patient who experienced hyperprogression, and pre-treatment imagery of a patient who did not respond to immunotherapy; and
testing the second machine learning classifier to discriminate between patients who experienced hyperprogression and patients who responded to immunotherapy using a second testing set of imagery, where the second testing set includes pre-treatment imagery of a patient who experienced hyperprogression, and pre-treatment imagery of a patient who responded to immunotherapy.

14. The non-transitory computer-readable storage device of claim 12, where selecting the first set of discriminative features includes selecting the first set of discriminative features using a minimum redundancy maximum relevance (mRMR) feature selection approach; and where selecting the second set of discriminative features includes selecting the second set of discriminative features using an mRMR feature selection approach.

15. The non-transitory computer-readable storage device of claim 1, the operations further comprising:
generating a first personalized cancer treatment plan based on the first classification and displaying the first personalized cancer treatment plan; or
generating a second personalized cancer treatment plan based on the second classification and displaying the second personalized cancer treatment plan.

16. An apparatus for distinguishing hyperprogressors (HPs) from responders (R) or non-responders (non-R) in non-small cell lung cancer (NSCLC), the apparatus comprising:
a processor;
a memory configured to store a digitized image of a region of tissue demonstrating cancerous pathology, the image including a plurality of pixels, a pixel having an intensity;
an input/output (I/O) interface;
a set of circuits; and
an interface that connects the processor, the memory, the I/O interface, and the set of circuits, the set of circuits comprising:
an image acquisition circuit configured to:
access a pre-immunotherapy treatment digitized computed tomography (CT) image of a region of tissue demonstrating non-small cell lung cancer (NSCLC), the image including a plurality of pixels, a pixel having an intensity, where the region of tissue includes a tumoral region;
define a tumoral boundary by segmenting the tumoral region represented in the image; and define a peritumoral region based on the tumoral boundary, where the peritumoral region includes a plurality of annular rings;

a radiomic feature circuit configured to:
extract a first set of radiomic features from the peritumoral region; and
extract a second set of radiomic features from the peritumoral region and the tumoral region;

a first classification circuit configured to:
compute a first probability, based on the first set of radiomic features, that the region of tissue is a hyperprogressors (HP) or non-responder (non-R) to immunotherapy; and
generate a first classification of the region of tissue as HP or non-R based on the first probability;

a second classification circuit configured to:
determine if the first probability that the region of tissue is HP or non-R is not within a threshold level;
upon determining that the first probability that the region of tissue is HP or non-R is not within a threshold level:
compute a second probability, based on the second set of radiomic features, that the region of tissue is a hyperprogressors (HP) or responder (R) to immunotherapy;
generate a second classification of the region of tissue as HP or R based on the second probability; and a display circuit configured to:
display the first classification or the second classification; and
display the image.

17. The apparatus of claim 16, where:
the first set of radiomic features includes:
a standard deviation of a peritumoral Laws level-spot feature extracted from a 0 mm-3 mm annular ring;
a range of a peritumoral Gabor feature having a frequency of zero and a theta of zero, extracted from a 3 mm-6 mm annular ring;
a kurtosis of a peritumoral Gabor feature having a frequency of two and a theta of zero, extracted from a 3 mm-6 mm annular ring;
a skewness of a peritumoral Haralick correlation extracted from a 3 mm-6 mm annular ring; and
a kurtosis of a peritumoral co-occurrence of local anisotropic gradient entropy inertia feature extracted from a 3 mm-6 mm annular ring;
and where the second set of radiomic features includes:
a kurtosis of a tumoral Laws spot-spot feature;
a range of a peritumoral Gabor feature having a frequency of zero and a theta of zero, extracted from a 3 mm-6 mm annular ring;
a kurtosis of a peritumoral Laws level-level feature extracted from a 3 mm-6 mm annular ring;
a mean of a peritumoral Laws ripple-edge feature extracted from a 3 mm-6 mm annular ring; and
a mean of a peritumoral Laws ripple edge feature extracted from a 9 mm-12 mm annular ring.

18. The apparatus of claim 16, where:
the first classification circuit is configured as a linear discriminant analysis (LDA) classifier trained to compute the first probability based on the first set of radiomic features; and where
the second classification circuit is configured as an LDA classifier trained to compute the second probability based on the second set of radiomic features.

19. The apparatus of claim 16, the set of circuits further comprising:
a training circuit configured to:
access a set of imagery acquired of a plurality of patients demonstrating NSCLC, where each patient has received three or fewer cycles of immunotherapy treatment and developed progressive NSCLC within the three or fewer cycles of immunotherapy treatment, where for each patient, the set of imagery includes a pre-baseline image acquired at a first time, a baseline image acquired at a second time later than the first time, and a post-treatment image acquired at a third time later than the second time, where the pre-baseline image, the baseline image, and the post-treatment image each include a tumoral region and a peritumoral region, the tumoral region having a boundary and an area;
compute, for each patient respectively, a pre-treatment tumor growth kinetics (TGK) value;
compute, for each patient respectively, a post-treatment TGK value;
compute for each patient, respectively, a ratio of the post-treatment TGK value to the pre-treatment TGK value;
classify a patient as a hyperprogressor (HP) where the ratio of the post-treatment TGK value to the pre-treatment TGK value is greater than or equal to two;
extract a set of radiomic features from the tumoral region and the peritumoral region of the baseline imagery;
select, using a minimum redundancy, maximum relevance (mRMR) feature selection approach, a first set of discriminative features from the set of radiomic features that discriminate between hyperprogressors and non-responders;
select, using an mRMR feature selection approach, a second set of discriminative features from the set of radiomic features that discriminate between hyperprogressors and responders;
train the first classification circuit to discriminate between hyperprogressors and non-responders using the first set of radiomic features and a first training set of imagery, where the first training set includes pre-treatment imagery of a patient who experienced hyperprogression, and pre-treatment imagery of a patient who did not respond to immunotherapy; and
train the second classification circuit to discriminate between hyperprogressors and responders using the second set of radiomic features and second training set of imagery, where the second training set includes pre-treatment imagery of a patient who experienced hyperprogression, and pre-treatment imagery of a patient who responded to immunotherapy; and a testing circuit configured to:
test the first classification circuit to discriminate between patients who experienced hyperprogression and patients who did not respond to immunotherapy using a first testing set of imagery, where the first testing set includes pre-treatment imagery of a patient who experienced hyperprogression, and pre-treatment imagery of a patient who did not respond to immunotherapy; and
test the second classification circuit to discriminate between patients who experienced hyperprogression and patients who responded to immunotherapy using a second testing set of imagery, where the second testing set includes pre-treatment imagery of a patient who experienced hyperprogression, and pretreatment imagery of a patient who responded to immunotherapy.

20. A non-transitory computer-readable storage device storing computer-executable instructions that when executed control a computer to perform a method of distinguishing hyperprogressors from other patterns of response in non-small cell lung cancer (NSCLC), the method comprising:

accessing a digitized pre-immunotherapy treatment computed tomography (CT) image of a region of tissue demonstrating NSCLC pathology, the image including a plurality of pixels, a pixel having an intensity;

defining a tumoral boundary by segmenting a tumoral region represented in the image;

defining a peritumoral region based on the tumoral boundary, where the peritumoral region includes a plurality of annular rings;

extracting a first set of radiomic features from the peritumoral region;

providing the first set of radiomic features to a first linear discriminant analysis (LDA) classifier trained to distinguish hyperprogressors (HP) from non-responders (non-R);

receiving a first probability from the first LDA classifier that the region of tissue is HP or non-R;

upon determining that the first probability that the region of tissue is HP or non-R is within a threshold level:
generating a first classification of the region of tissue as HP or non-R based on the first probability; and
displaying the first classification;

upon determining that the first probability that the region of tissue is HP or non-R is not within the threshold level:
extracting a second set of radiomic features from the peritumoral region and the tumoral region;
providing the second set of radiomic features to a second LDA classifier trained to distinguish HPs from responders (R);
receiving a second probability from the second LDA classifier that the region of tissue is HP or R;
generating a second classification of the region of tissue as HP or R based on the second probability; and
displaying the second classification.

* * * * *

UNITED STATES PATENT AND TRADEMARK OFFICE
CERTIFICATE OF CORRECTION

PATENT NO. : 10,839,513 B2
APPLICATION NO. : 16/297889
DATED : November 17, 2020
INVENTOR(S) : Pranjal Vaidya et al.

Page 1 of 1

It is certified that error appears in the above-identified patent and that said Letters Patent is hereby corrected as shown below:

In the Specification

Column 1, Lines 16 through 22; please replace "This invention was made with government support under grants 1U24CA199374-01, R01CA202752-01A1, R01CA208236-01A1, R01CA216579-01A1, R01CA220581-01A1, and 1 C06RR12463-01 awarded by the National Institutes of Health. Also award W81XWH-16-1-0329 awarded by the Department of Defense. The government has certain rights in the invention." with --This invention was made with government support under grants CA199374, CA202752, CA208236, CA216579, CA220581, and RR012463 awarded by the National Institutes of Health; and grant(s) W81XWH-16-1-0329 awarded by the Department of Defense. The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*